(12) United States Patent
Garcia Lopez et al.

(10) Patent No.: US 9,297,034 B2
(45) Date of Patent: Mar. 29, 2016

(54) DETECTION OF STREPTOCOCCUS PNEUMONIAE THROUGH MAGNETO-AMPEROMETRIC GENOSENSORS USING LYTA GENE-SPECIFIC PRIMERS AND PROBES

(75) Inventors: Ernesto Garcia Lopez, Madrid (ES); Pedro Garcia Gonzalez, Madrid (ES); José Luis Garcia Lopez, Madrid (ES); Susana Campuzano Ruiz, Madrid (ES); María Morales Areizaga, Madrid (ES); María Carmen Ardanuy Tisaire, L'hospitalet de Llobregat (ES); José Manuel Pingarrón Carrazón, Madrid (ES); María Pedrero Muñoz, Madrid (ES)

(73) Assignees: Consejo Superior de Investigaciones Científicas (CSIC, Madrid (ES); Centro de Investigación Biomédica en Red de Enfermedades, Islas Baleares (ES); Universidad Complutense de Madrid, Madrid (ES)

( * ) Notice: Subject to any disclaimer, the term of this patent is extended or adjusted under 35 U.S.C. 154(b) by 147 days.

(21) Appl. No.: 13/516,617

(22) PCT Filed: Dec. 16, 2010

(86) PCT No.: PCT/ES2010/070836
§ 371 (c)(1),
(2), (4) Date: Nov. 9, 2012

(87) PCT Pub. No.: WO2011/073488
PCT Pub. Date: Jun. 23, 2011

(65) Prior Publication Data
US 2013/0052641 A1    Feb. 28, 2013

(30) Foreign Application Priority Data
Dec. 16, 2009   (ES) .................................. 200931177

(51) Int. Cl.
*C12Q 1/68* (2006.01)
*C12P 19/34* (2006.01)
*C07H 21/04* (2006.01)

(52) U.S. Cl.
CPC ............ *C12Q 1/6825* (2013.01); *C12Q 1/6888* (2013.01); *C12Q 1/689* (2013.01); *C12Q 2563/143* (2013.01); *C12Q 2565/607* (2013.01)

(58) Field of Classification Search
CPC ........... C12Q 1/6825; C12Q 2531/113; C12Q 1/6888; C12Q 1/689; C12Q 2563/143; C12Q 2565/607
See application file for complete search history.

(56) References Cited

U.S. PATENT DOCUMENTS 6,391,558 B1 *  5/2002  Henkens et al. ............. 435/6.11
2009/0087837 A1  4/2009  Seki et al.

FOREIGN PATENT DOCUMENTS

| WO | WO 2007/106407 | * | 9/2007 |
| WO | WO 2009011971 | * | 1/2009 |
| WO | WO-2009011971 A2 | | 1/2009 |

OTHER PUBLICATIONS

Loaiza (Analyst 2009 vol. 134 pp. 34-37 pre-published online Nov. 4, 2008).*
Loaiza (Anal Chem 2008 vol. 80 pp. 8239-8245).*
Carvalho M., et al, Evaluation and Improvement of Real-time PCr Assays Targeting lytA, ply and psaA genes for detection of Pnumococcal DNA Journal of Clinical Microbiology (2007), vol. 45, No. 8, pp. 2460-2466.
Hernandez-Santos D., et al., Genosensor Based on a Platinum(II) Complex as Electrocatalytic Label, Anal. Chem. (2005), vol. 77, No. 9, pp. 2868-2874.
Lermo A., et al., In situ DNA Amplification with Magnetic Primers for the Electrochemical Detection of Food Pathogens, Biosensors and Bioelectronics (2007), vol. 22, No. 9-10, pp. 2010-2017.
McAvin J.C. et al., Sensitive and Specific Method for Rapid Detection of *Streptococcus pneumoniae* Using Real-time Fluorescence PCR, Journal of Clinical Microbiology (2001), vol. 39, No. 10, pp. 3446-3451.
Sheppard C.L. et al., Autolysin-targeted LightCycler Assay Including Internal Process Control for Detection of *Streptococcus pneumoniae* DNA in Clinical Samples, Journal of Medical Microbiology (2004), vol. 54, pp. 189-195.
International Search Report issued in PCT/ES2010/070836 on May 24, 2011.

(Continued)

*Primary Examiner* — Amanda Haney
(74) *Attorney, Agent, or Firm* — Danielle L. Herritt; Jill Ann Mello

(57) ABSTRACT

The present invention relates to a method for the detection and/or quantification of *Streptococcus pneumoniae*, a Gram-positive bacteria that is an important human pathogen, in an isolated biological sample, through magneto-amperometric biosensors, comprising detecting fragments of lytA gene of the microorganism, amplified through PCR, preferably asymmetric PCR or direct asymmetric PCR, by hybridization thereof to a specific probe fully complementary to a region of the amplified fragment. Furthermore, the present invention also relates to the use of primers SEQ ID NO: 3 and 4 together with probes SEQ ID NO: 1 and/or SEQ ID NO: 2 to perform the detection. The biosensor developed to detect *S. pneumoniae* can be applied to different types of clinical samples from patients infected with this bacterium or other related bacteria. Preferably the clinical sample is an isolated biological fluid such as blood, cerebrospinal fluid, saliva or urine.

8 Claims, 6 Drawing Sheets

(56) References Cited

OTHER PUBLICATIONS

Brouwer, et al., Host Genetic Suscepibility to Pneumococcal and Meningococcal Disease: a Systematic Review and Meta-analysis, www.thelancet.com/infection vol. 9, Jan. 2009.

Dochez, et al., The Elaboration of Specific Soluble Substance by Pneumococcus During Growth, downloaded from jern.rupress.org on May 24, 2010.

Ehara, et al., A Novel Method for Rapid Detection of *Streptococcus pneumoniae* Antigen in Sputum and Its Application in Adult Respiratory Tract Infections, Journal of Medical Microbiology (2008) 57, 820-826.

Erdem, et al., Electrochemical Genomagnetic Assay for the Detectgion of Hepatitis B virus DNA in polymerase Chain Reaction Amplicons by Using Disposable Sensor Technology, Electrochemistry Communications 7 (2005) 815-820.

Gabig-Ciminska, et al., Electric Chips for Rapid Detection and Quantification of Nucleic Acids, Biosensors and Bioelectronics 19 (2004) 537-546.

Klugman, et al., Novel Approaches to the Identification of *Streptococcus pneumoniae* as the Cause of Community-Acquired Pneumonia, CID 2008:47 (Suppl 3) S202-S206.

Lermo, et al., Towards Q-PCR of Pathogenic Bacteria with Improved Electrochemical Double-tagged Genosensing Detection, Biosensors and Bioelectronics 23 (2008) 1805-1811.

Lin, et al., Magnetic Beads-based Bioelectrochemical Immunoassay of Polycyclic Aromatic Hydrocarbons, Electrochemistry Communications 9 (2007) 1547-1552.

Lode, et al., Clinical Impact of Antiobiotic-resistant Gram-positive Pathogens, clin Microbial Infect 2009; 15:212-217.

Lucarelli, et al., Electrochemical and Piezoelectric DNA Biosensors for Hybridisation Detection, Analytica Chimica Acta 609 (2008) 139-159.

Rai, et al., Development of a Sandwich dot-enzyme Linked Immunosorbent Assay for *Streptococcus pneumoniae* Antigen Detection in Cerebrospinal Fliud, Comparative Immunology, Microbiology & Infectious Diseases 27 (2004) 217-223.

Samra, et al., Use of the NOW *Streptococcus pneumoniae* Urinary Antigen Test in Cerebrospinal Fluid for Rapid Diagnosis of Pneumococcal Meningitis, Diagnostic Microbiology and Infectious Disease, 45 (2003) 237-240.

Scott, The Preventable Burden of Pneumococcal Disease in the Developing World, Vaccine 25 (2007) 2398-2405.

Stuertz, et al., Enzyme Immunoassay Detecting Teichoic and Lipoteichoic Acids versus Cerebrospinal Fliud Culture and Latex Agglutination for Diagnosis of *Streptococcus pneumoniae* Meningitis, Journal of Clinical Microbiology, Aug. 1998, p. 2346-2348.

Wang, et al., Magnetic Bead-Based Label-Free Electrochemical Detection of DNA Hybridization, Analyst, 2001, 126, 2020-2024.

Werno, et al., Laboratory Diagnosis of Invasive Pneumococcal Disease, CID 2008:46 (Mar. 15) Medical Microbiology.

World Health Organization Geneva, Weekly Epidemiological Record, Pneumococcal Conjugate Vaccine for Childhood Immunization—WHO position paper, Mar. 23, 2007, 82nd Year, No. 12, 2007, 82, 93-104.

* cited by examiner

*lytA* Amplicon (235 bases)

*lytA* Amplicon (235 bp)

DETECTION OF STREPTOCOCCUS PNEUMONIAE THROUGH MAGNETO-AMPEROMETRIC GENOSENSORS USING LYTA GENE-SPECIFIC PRIMERS AND PROBES

This application is the U.S. national phase of International Application No. PCT/ES2010/070836, filed on Dec. 16, 2010, which claims the benefit of Spanish Patent Application No. P200931177, filed Dec. 16, 2009.

The present invention relates to a method for the detection and/or quantification of *Streptococcus pneumoniae*, a Gram-positive bacteria which is an important human pathogen, in an isolated biological sample, through magneto-amperometric biosensors, comprising detecting fragments of the lytA gene of said microorganism, amplified through PCR, preferably asymmetric PCR or direct asymmetric PCR, by means of the hybridization thereof to a specific probe fully complementary to a region of said amplified fragment. Furthermore, the present invention also relates to the use of primers SEQ ID NO: 3 and 4, together with probes SEQ ID NO: 1 and/or SEQ ID NO: 2, to perform said detection. The biosensor developed to detect *S. pneumoniae* makes it possible to be applied to different types of clinical samples obtained from patients infected with this bacterium or other related bacteria. Preferably, the clinical sample is an isolated biological fluid such as blood, cerebrospinal fluid, saliva or urine.

PREVIOUS STATE OF THE ART

*Streptococcus pneumoniae* (*S. pneumoniae*), or pneumococcus, is a Gram-positive bacterium producing an α-hemolytic reaction, when incubated in the appropriate means. Pneumococcus is a pathogen that causes a great number of serious infections (pneumonia, meningitis, acute otitis media, bacteremia, etc.), mainly in children, elderly people and immunocompromised people. Taken together, the death rate due to this microorganism is higher than that produced by any other pathogenic bacteria, particularly in developing countries (Scott, 2007. Vaccine, 25: 2398-2405.)

Invasive pneumococcal disease, defined as pneumonia, bacteremia, or meningitis, is one of the main causes of morbidity and mortality in the world. Pneumococcus is the cause of death, yearly, for more than one million children under the age of 5 worldwide, many of them due to pneumonia (WHO, 2007. Wkly. Epidemiol. Rec., 82: 93-104.) *S. pneumoniae* is the main cause of community-acquired pneumonia and bacterial meningitis, at least in developed countries (Brouwer et al., 2009. Lancet Infect. Dis., 9: 31-44.). Pneumococcal pneumonia has a death rate of up to 30%, depending on the existence of concomitant bacteremia, as well as the patients age and underlying diseases. When it is not properly diagnosed and treated, pneumococcal pneumonia can produce bacteremia and meningitis. When there is clinical suspicion of pneumonia, an empiric treatment with broad-spectrum antibiotics is usually applied, which can lead to the indiscriminate use of antibiotics, a practice that has been proven to increase bacterial resistance and to which almost all health centers have expressed their opposition. In fact, the increased resistance to antibiotics of pneumococcal clinical isolates is a worldwide health problem (Lode, 2009. Clin. Microbiol. Infect., 15: 212-217.).

Conventional methods used to diagnose pneumonia and the invasive pneumococcal disease in general, based on the culture of respiratory or blood samples, require time and are often complex and imperfect (Werno y Murdoch, 2008. Clin. Infect. Dis., 46: 926-932.). In many patients, the etiology remains hidden after the usual diagnostic procedure. Classification based in the culture of sputum specimen is controversial due to the oropharyngeal carriage of pneumococci present in healthy carriers or because of inadequate sputum specimens, thus contributing to an undetermined number of false positives. The result of the culture, after the Gram stain, normally requires 48 hours, which together with the already known sensitivity and specificity problems, makes the method uneconomical. Like the sputum specimen culture, the blood culture also suffers from delay and low sensitivity problems. On the other hand, serology requires sera from convalescent patients to record an antibody titer increase and usually does not provide diagnosis information early enough to be clinically relevant. Pneumococcal pneumonia diagnosis through blood culture is only useful in the 10%-30% of patients suffering from pneumococcal pneumonia who develop bacteremia. Invasive samples, such as those obtained through broncoalveolar lavage or transtracheal aspiration, are generally considered the most reliable ones to determine the etiology of pneumonia, and the isolation of pneumococci from these samples proves the pneumococcal origin. However, those are invasive techniques, which require trained personnel, which are not free of complications and which, therefore, are not routinely used in the diagnosis (Werno and Murdoch, 2008. Clin. Infect. Dis., 46: 926-932.).

The development of simple methods for determining the presence of pneumococcal antigens in urine (antigenuria) over the past few years has represented an important advance by solving part of the aforementioned problems. The recent interest in the urinary test responds to the fact that the microbial antigens are more concentrated in the urine than in other fluids and that there exist no antibodies in it that may alter the results. The detection of pneumococcal antigens (habitually capsular polysaccharides) in urine was already described in 1917 (Dochez and Avery, 1917. J. Exp. Med., 26: 477-493.). Since then there has been attempts to analyze it using different techniques such as counterimmunoelectrophoresis, latex agglutination, co-agglutination, enzyme immunoassay, etc. and some other methodologies (Rai et al., 2004. Comp. Immunol. Microbiol. Infect. Dis., 27: 217-223; Samra et al., 2003. Diagn. Microbiol. Infect. Dis., 45: 237-240; Stuertz et al., 1998. J. Clin. Microbiol., 36: 2346-2348.).

In the late nineties, a simple and fast method (Binax NOW®) based on immunochromatographic membrane assay was developed for the presumptive diagnosis of pneumococcal pneumonia. This method detects the C polysaccharide (a teichoic acid containing choline), characteristic not only of all pneumococci, but also of pathogens such as *Streptococcus pseudopneumoniae, Streptococcus mitis* and *Streptococcus oralis*, in the urine of infected patients. Although the Binax NOW is positive for the 23 serotypes of pneumococcus responsible for 90% of the severe pneumococcal infections and provides results in only 15 minutes, it has a high detection limit [≅$1.0 \times 10^5$ colony-forming units (cfu) ml$^{-1}$], poor selectivity towards other streptococci (*S. mitis, S. oralis* and other α-hemolytic streptococci) and other pathogenic bacteria (*Haemophilus influenzae, Staphylococcus aureus* and, sometimes, *Escherichia coli*), and has limited reliability in pediatric patients because they are often carriers of the germ and due to the increasing vaccination among the child population (Werno and Murdoch, 2008. Clin. Infect. Dis., 46: 926-932.). Furthermore, this test is associated both with the lack of detection immediately after the onset of the infection, and with the appearance of positive long-term results despite treatment (1-3 months) or 48 hours after vaccination (Ehara et al., 2008. J. Med. Microbiol., 57: 820-826.).

Over the past few years, there have been developed new methods for microbial identification which incorporate technologies based on molecular biology and, more specifically, on variations of the polymerase chain reaction or PCR technique, which, at least in principle, should provide higher sensitivity and specificity as well as, ideally, higher speed and lower costs (Klugman et al., 2008. Clin. Infect. Dis., 47:S202-S206; Werno y Murdoch, 2008. Clin. Infect. Dis., 46: 926-932.). On the other hand, the development of methods based on biosensors is of great interest nowadays since they lead to results that are as reliable as those of traditional assays, based on cultures and colony counts, but in much shorter time. However, it is still necessary to achieve the same detection levels reached by traditional methodologies (10-100 cfu $ml^{-1}$). Particularly, DNA sensors, also known as genosensors, based on the integration of a sequence-specific probe (usually a short-chain synthetic oligonucleotide) and an electrochemical transducer, are considered to be the most appealing approach currently, due to its simplicity, the low cost of the required instruments and the possibility of an accurate detection in real time with very low detection limits (Lucarelli et al., 2008. Anal. Chim. Acta, 609: 139-159.). Furthermore, it is still necessary to carry out the sample amplification through PCR, due to the poor abundance and extreme complexity of analytes without amplification. Similarly, it is necessary to develop new designs of probes and procedures for carrying out the pretreatment of the samples which allow the process of biorecognition taking place in the transducer-dissolution interface to be truly effective.

The superparamagnetic particles (MBs) constitute a versatile tool for the development of genosensors. In fact, these particles provide a large surface area for the immobilization of probes, which may thus be easily separated from the liquid phase with a small magnet, and dispersed again immediately when it is removed (Erdem et al., 2005. Electrochem. Commun., 7: 815-820, Gabig-Ciminska et al., 2004. Biosens. Bioelectron, 19: 537-546). Furthermore, the particles which are not specifically bound may be automatically removed by magnetically controlled washing (Lin et al., 2007. Electrochem. Commun., 9: 1547-1552), thus demonstrating its usefulness for purification and preconcentration purposes (Lin et al., 2007. Electrochem. Commun., 9: 1547-1552; Wang et al., 2001. Analyst, 126: 2020-2024.).

Over the past few years, different research groups have worked extensively in the design and development of new amperometric genosensors, based on the use of modified MBs and graphite-epoxy composite magneto electrodes, applicable to the detection of pathogenic bacteria (*Salmonella* sp. and *E. coli* 0157:H7) for food control (Lermo et al., 2007. Biosens. Bioelectron., 22: 2010-2017; Lermo et al., 2008. Biosens. Bioelectron., 23: 1805-1811.)

DESCRIPTION OF THE INVENTION

The present invention relates to the development of sensitive and selective electrochemical biosensors (based on the use of disposable printed electrodes, superparamagnetic particles (MBs), DNA-specific probes and DNA asymmetric amplification strategies for fast detection and identification of pneumococci, encapsulated or not, related to pneumococcal infections in several samples, including clinical samples.

The methodology described in the present invention takes just a few hours ($\cong$5.5 h) (in contrast to the 2-3 days required by analyses based on culture techniques) and uses low cost reagents. The sensors developed have proven to be useful for the fast, specific, quantitative and sensitive detection of amplified fragments (hereinafter called "amplicon" or "amplification product") obtained directly from the cultures of *Streptococcus pneumoniae* (*S. pneumoniae*) without using complex procedures for treating the sample. Furthermore, the use of these hybridization sensors also prevents one of the main disadvantages of analyses using PCR, such as false positives. By using this methodology, a detection limit of 1,1 nM has been reached for amplicons obtained through asymmetric PCR (aPCR) from genomic DNA of *S. pneumoniae* R6, which means that up to 30 sensors per day can be manufactured and used. The system developed has also been used successfully in the fast, specific and sensitive detection of the products obtained through asymmetric direct PCR (aDPCR) from cultures of *S. pneumoniae* and, thus, simplifying even more the procedures for treating the sample. The coupling of the hybridization magnetic sensors with aDPCR allows the selective detection of only 100 cfu $ml^{-1}$ of the R6 strain of *S. pneumoniae*, showing the practical usefulness of said method for the assessment of clinical samples. Furthermore, the use of mass-produced disposable screen-printed electrodes allows the analysis of several samples per day with short assay times. These features are important for the application of the developed genosensors to the detection, in clinical samples, of *S. pneumoniae* and related species. The results obtained also show that the genosensors, besides acting as an alarm device for the control of clinical samples, allow the quantitative detection of pneumococcus.

Given the interest involved in the fast and unequivocal detection of the presence of low concentrations of pneumococcus in different clinical samples to begin the most suitable treatment as soon as possible, the methodology proposed in the present invention solves the technical problem of detecting the microorganisms of the *S. pneumoniae* species in clinical samples where, preferably, said samples are from different body fluids: blood, urine, cerebrospinal fluid, pleural fluid or from specific locations such as the nasopharynx or the conjunctiva.

The design of the *S. pneumoniae*-specific probe and primer sequences has been carried out thanks to the sequencing of the lytA gene from 115 clinical isolates of pneumococcus which are neither published nor included in any public data base, so that, thanks to the results obtained in said sequencing, it has been possible to provide a solution to a technical problem that had not yet been solved, with the objective of detecting in a fast and effective manner the bacterial agent causing pneumonia, bacteremia or meningitis, one of the main causes of morbidity and mortality in the world.

One aspect of the present invention relates to a method for the detection and/or quantification of *Streptococcus pneumoniae* in an isolated biological sample, by means of magnetoamperometric biosensors, comprising:

a. immobilizing on a solid support a suspension of MBs labeled with a compound A and with the probe of DNA SEQ ID NO: 1 labeled on its 5' end with a compound B related to compound A, where said particles and probe are bound by the binding of compounds A-B, b. adding to the mixture of step (a) the product of the amplification through PCR obtained by using the direct primer SEQ ID NO: 3 and the reverse primer SEQ ID NO: 4 of the lytA gene of *S. pneumoniae*, from an isolated biological sample, where the primer SEQ ID NO: 4 is bound by its 5' end to the compound B, and c. detecting the hybridization of the probe SEQ ID NO: 1 of step (a) to the DNA fragment amplified in step (b), by adding the compound A conjugated to an element capable of being detected and/or quantified.

The term "biological sample" refers to an isolated sample of material of biological origin that may be both of human or animal origin. This method can be applied mainly to samples of human origin, but the method of the present invention may also be applied to the detection of this microorganism in other living creatures that may act as vehicles for transmitting said microorganism. The biological sample may be selected from the list comprising biological fluid or tissue biopsy. The biological fluid may be, but is not limited to, a respiratory sample, bone marrow aspirations, cerebrospinal fluid, urine or blood fluid. Blood fluid means blood, serum or plasma.

The term "compound B related to compound A" refers to the tendency of said compounds A and B to combine with each other, that is, to be bound or attached by at least one kind of chemical bond of any type.

The term "element capable of being detected and/or quantified" refers to a component that can react with a substrate, so that an isotopic, colorimetric, fluorometric or electrochemical detection is derived thereof. This element is directly bound to element A, or through another compound. An example of the element capable of being detected and/or quantified is, but is not limited to, the horseradish peroxidase (HRP) enzyme, chromogenic substrate marker, such as, the tetramethylbenzidine (TMB), the azino-bis(3-ethylbenzthiazoline-6-sulphonic acid) or the phenylenediamine, not limited to those and being possible to use other substrates.

A preferred embodiment relates to a method for the detection and/or quantification of S. pneumoniae, by means of magneto-amperometric biosensors, where the biological sample is an isolated biological fluid. A more preferred embodiment relates to a method for the detection and/or quantification of S. pneumoniae, by means of magneto-amperometric biosensors, where the isolated biological fluid is blood, cerebrospinal fluid, saliva or urine.

Another preferred embodiment relates to a method for the detection and/or quantification of S. pneumoniae, by means of magneto-amperometric biosensors, where the PCR is asymmetric. According to a more preferred embodiment, an amount of the primer SEQ ID NO: 3 is used that is between 8 and 12 times smaller than the primer SEQ ID NO: 4, bound by its 5' end to compound B. Preferably, an amount of the primer SEQ ID NO: 3 is used that is 10 times smaller than the primer SEQ ID NO: 4, bound by its 5' end to compound B.

Asymmetric PCR (aPCR) is a technique for the amplification of DNA fragments through PCR that produces single-stranded fragments by using the two necessary primers at different molar concentrations. In this way, double-stranded DNA is produced exponentially until the minority primer is exhausted and then only the chain that hybridizes with the excess DNA is produced, being produced thereafter on a linear basis. In this way, the product of PCR contains more single-stranded DNA than double-stranded DNA, which allows the single-stranded DNA to be used to hybridize with a DNA probe immobilized on a support. Said single-stranded DNA amplified through aPCR must be bound to compound B by its 5' end.

A more preferred embodiment relates to a method for the detection and/or quantification of S. pneumoniae, by means of magneto-amperometric biosensors, where the asymmetric PCR is direct. The direct asymmetric PCR (aDPCR) refers to the aPCR technique in which the template DNA has not been extracted, thereby reducing the detection time and avoiding the unnecessary use of reagents. The critical step of this type of technique is the efficiency in the permeation of the cells to free the DNA to enable it to hybridize with the aforementioned specific primers.

Another preferred embodiment relates to a method for the detection and/or quantification of S. pneumoniae, by means of magneto-amperometric biosensors, where compound A conjugated to an element capable of being detected and/or quantified according to step (c) is, in turn, covalently conjugated to a hydrophilic polymer backbone.

According to another preferred embodiment, in the method for the detection and/or quantification of S. pneumoniae, by means of magneto-amperometric biosensors, compound A is streptavidin and compound B is biotin.

Another preferred embodiment relates to a method for the detection and/or quantification of S. pneumoniae, by means of magneto-amperometric biosensors, where the element capable of being detected and/or quantified according to step (c) is an oxidase enzyme. According to a more preferred embodiment, the element capable of being detected and/or quantified according to step (c) is the peroxidase enzyme and said detection and/or quantification is carried out by adding $H_2O_2$.

Another preferred embodiment relates to a method for the detection and/or quantification of S. pneumoniae, by means of magneto-amperometric biosensors for monitoring the response to a S. pneumoniae treatment.

The monitoring procedure comprises a series of steps that begin with a serial sampling. Serial sampling means the extraction of any type of biological samples, including those mentioned in this invention. The sampling is carried out at different times from the moment when the treatment is administered, so that the quantification of the amplification of the fragments obtained from samples from the same patient will show the efficiency of said treatment. Thus, a decrease in the concentration of the amplification product vis-à-vis the control values, the latter represented, for example, by amplification values in a same individual, prior to the treatment, would mean that the treatment is taking effect in the sense of decreasing the number of microorganisms causing the disease. This example would not be limited to the use of this type of control.

Another aspect of the present invention relates to the use of the direct primer SEQ ID NO: 3 and the reverse primer SEQ ID NO: 4 for the amplification through PCR of a DNA fragment of lytA gene of S. pneumoniae and its detection and/or quantification with the probe SEQ ID NO: 1 and/or with the probe SEQ ID NO: 2, where said probes have a labeling that allows an isotopic, colorimetric, fluorometric or electrochemical detection, using as a template the DNA present in an isolated biological sample. According to a preferred embodiment, said probes have a labeling that allows an electrochemical detection. SEQ ID NO: 2 is the sequence of the target probe, complementary to the capture probe SEQ ID NO: 1 and, therefore, it may be used as a positive control of the technique performance.

The isotopic detection comprises the detection of a radioactive isotope with which the probe is labeled, where the isotope may be for example, without being limited to, a radioactive isotope of phosphorus (such as, but not limited to, $P^{32}$) or a radioactive isotope of hydrogen (such as, but not limited to, tritium; $H^3$.) The colorimetric or chromogenic detection refers to the detection of the appearance of a color which intensity varies in a manner directly proportional to the amount of fragments with which the labeled probe hybridizes. In the case of the colorimetric detection the probe is labeled with, for example, but not limited to, a substrate capable of reacting with one of the components thereby producing a compound that may be detected by, for example, but not limited to, spectrophotometry or colorimetry. The fluorometric detection is carried out by means of the detection of a probe labeled with a fluorogenic substrate using fluorometry. The electrochemical detection relates to species capable of being oxidized or reduced on the surface of electrodes or which, through certain reactions or modifications, produce electroactive species.

A preferred embodiment relates to the use of said primers for the amplification through PCR of a DNA fragment of the lytA gene of *S. pneumoniae* and its detection and/or quantification by means of the probe SEQ ID NO: 1 and/or with the probe SEQ ID NO: 2, where the isolated biological sample is an isolated biological fluid. A more preferred embodiment relates to said use, where the isolated biological fluid is blood, cerebrospinal fluid, saliva or urine.

Another preferred embodiment relates to the use of said primers for the amplification through PCR of a DNA fragment of the lytA gene of *S. pneumoniae* and its detection and/or quantification by means of the probe SEQ ID NO: 1 and/or with the probe SEQ ID NO: 2, where the PCR is asymmetric. According to a more preferred embodiment, the asymmetric PCR is direct.

Another aspect of the present invention relates to the use of said primers for the amplification through PCR of a DNA fragment of the lytA gene of *S. pneumoniae* and its detection and/or quantification by means of the probe SEQ ID NO: 1 and/or with the probe SEQ ID NO: 2 for monitoring the response to a *S. pneumoniae* treatment.

Another aspect of the present invention relates to the use of a kit comprising the direct primer SEQ ID NO: 3, the reverse primer SEQ ID NO: 4, and the probe SEQ ID NO: 1 and/or the probe SEQ ID NO: 2, where said probes have a labeling that allows an isotopic, colorimetric, fluorometric or electrochemical detection, for the detection and/or quantification of *S. pneumoniae*.

Another aspect of the present invention relates to a kit comprising the direct primer SEQ ID NO: 3, the reverse primer SEQ ID NO: 4, and the probe SEQ ID NO: 1 and/or the probe SEQ ID NO: 2, where said probes have a labeling that allows an isotopic, colorimetric, fluorometric or electrochemical detection.

Another aspect of the present invention is the use of the kit described in the previous paragraph for monitoring the response to a treatment of *S. pneumoniae*, or the use of said kit for monitoring the response to a treatment of *S. pneumoniae*.

In the present invention, a capture probe and alternative couple of primers have been designed, which, coupled to the magneto-amperometric genosensors, allow the unequivocal identification of strains carrying the atypical alleles of lytA, characterizing other Streptococci of the Mitis group (SGM.) Thus, another aspect of the present invention relates to a method for the detection and/or quantification of streptococci of the mitis group (SGM) (*S. pseudopneumoniae, S. mills, S. oralis, S. sanguis* II and others) in an isolated biological sample, by means of magneto-amperometric biosensors, comprising:

a. immobilizing on a solid support a suspension of MBs labeled with a compound A and with the probe of DNA SEQ ID NO: 6 labeled on its 5' end with a compound B related to compound A, where said particles and probe are bound by the binding of compounds A-B,
b. adding to the mixture of step (a) the product of the amplification through PCR obtained by using the direct primer SEQ ID NO: 8 and the reverse primer SEQ ID NO: 9 of the lytA gene, from an isolated biological sample, where the primer SEQ ID NO: 9 is bound by its 5' end to compound B, and
c. detecting the hybridization of the probe SEQ ID NO: 6 of step (a) to the DNA fragment amplified in step (b), by adding the compound A conjugated to an element capable of being detected and/or quantified.

A preferred embodiment relates to a method for the detection and/or quantification of SGM, by means of magneto-amperometric biosensors, where the biological sample is an isolated biological fluid. A more preferred embodiment relates to a method for the detection and/or quantification of SGM, by means of magneto-amperometric biosensors, where the isolated biological fluid is blood, cerebrospinal fluid, saliva or urine.

Another preferred embodiment relates to a method for the detection and/or quantification of SGM, by means of magneto-amperometric biosensors, where the PCR is asymmetric. According to a more preferred embodiment, an amount of primer SEQ ID NO: 8 is used that is between 8 and 12 times smaller than primer SEQ ID NO: 9 bound by its 5' end to compound B. Preferably, an amount of primer SEQ ID NO: 8 is used that is 10 times smaller than primer SEQ ID NO: 9 bound by its 5' end to compound B.

A more preferred embodiment relates to a method for the detection and/or quantification of SGM, by means of magneto-amperometric biosensors, where the asymmetric PCR is direct. The direct asymmetric PCR (aDPCR) relates to the aPCR technique in which the template DNA has not been extracted, thereby reducing the detection time and avoiding the unnecessary use of reagents.

Another preferred embodiment relates to a method for the detection and/or quantification of SGM, by means of magneto-amperometric biosensors, where compound A conjugated to an element capable of being detected and/or quantified according to step (c) is in turn covalently conjugated to a hydrophilic polymer backbone.

According to another preferred embodiment, in the method for the detection and/or quantification of SGM, by means of magneto-amperometric biosensors, compound A is streptavidin and compound B is biotin.

Another preferred embodiment relates to a method for the detection and/or quantification of SGM, by means of magneto-amperometric biosensors, where the element capable of being detected and/or quantified according to step (c) is an oxidase enzyme. Preferably, the oxidase enzyme is a peroxidase and said detection and/or quantification is carried out by adding $H_2O_2$.

Another preferred embodiment relates to a method for the detection and/or quantification of SGM, by means of magneto-amperometric biosensors for monitoring the response to a *S. pneumoniae* treatment.

Another aspect of the present invention relates to the use of the direct primer SEQ ID NO: 8 and the reverse primer SEQ ID NO: 9 for the amplification through PCR of a DNA fragment of lytA gene of SGM and its detection and/or quantification with the probe SEQ ID NO: 6 and/or with the probe SEQ ID NO: 7, where said probes have a labeling that allows an isotopic, colorimetric, fluorometric or electrochemical detection, using as a template the DNA present in an isolated biological sample. SEQ ID NO: 7 is the sequence of the target probe, complementary to the capture probe SEQ ID NO: 6 and, therefore, it may be used as a positive control of the technique performance.

A preferred embodiment relates to the use of said primers for the amplification through PCR of a DNA fragment of the lytA gene of SGM and its detection and/or quantification by means of the probe SEQ ID NO: 6 and/or with the probe SEQ ID NO: 7, where the isolated biological sample is an isolated biological fluid. A more preferred embodiment relates to said use, where the isolated biological fluid is blood, cerebrospinal fluid, saliva or urine.

Another preferred embodiment relates to the use of said primers for the amplification through PCR of a DNA fragment of the lytA gene of SGM and its detection and/or quantification by means of the probe SEQ ID NO: 6 and/or with the probe SEQ ID NO: 7, where the PCR is asymmetric. According to a more preferred embodiment, the asymmetric PCR is direct.

Another aspect of the present invention relates to the use of the direct primer SEQ ID NO: 8 and/or SEQ ID NO: 9 for the amplification through PCR of a DNA fragment of the lytA gene of SGM and its detection and/or quantification with the probe SEQ ID NO: 6 and/or with the probe SEQ ID NO: 7 for monitoring the response to a SGM treatment.

Another aspect of the present invention relates to a kit comprising the direct primer SEQ ID NO: 8, the reverse primer SEQ ID NO: 9, and the probe SEQ ID NO: 6 and/or the probe SEQ ID NO: 7, where said probes have a labeling that allows an isotopic, colorimetric, fluorometric or electrochemical detection.

A preferred embodiment of the present invention relates to the use of the kit described in the previous paragraph for the detection and/or quantification of SGM, or for monitoring the response to an SGM treatment.

Throughout the description and the claims the word "comprise" and its variants are not intended to exclude other technical features, additives, components or steps. For those skilled in the art, other objects, advantages and features of the invention will be evident in part from the description and in part from the practice of the invention. The following drawings and examples are provided as an illustration, and are not intended to limit the present invention.

DESCRIPTION OF THE DRAWINGS

The following figures are shown as illustrative and non-limiting examples of the invention in order to complement the description above, as well as a way to help understand the characteristics of the invention according to some examples presented herein.

(1) probe-modified MB washing; (2) probe-target hybridization process or single-stranded biotinylated amplicon; (3) hybrid-modified MB separation and non-complementary oligonucleotide extraction; (4) enzymatic labeling with an ultra-sensitive streptavidin-HRP polymer; (5) capture of modified MBs on the gold-printed electrodes modified with tetrathiafulvalene (TTF-Au/SPEs); (6) amperometric detection of the mediated reduction of $H_2O_2$ with TTF.

Figure 2:
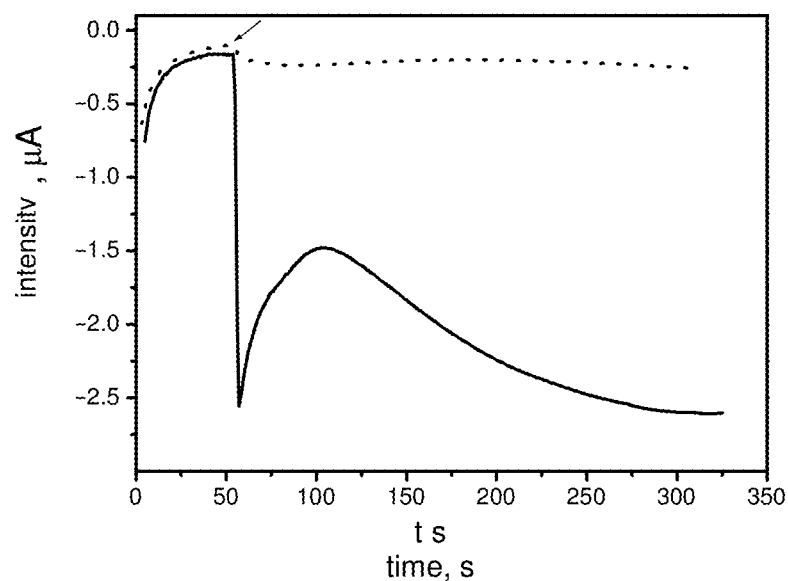

FIG. 2 Shows the amperograms obtained on the screen-printed electrodes modified with MBs after completing the hybridization process in the absence ( - - - ) and in the presence (–) of the biotinylated target probe.

Supporting electrolyte used, PBS (pH 7.4.) Experimental conditions: [immobilized probe]=1 µM; [complementary oligonucleotide]=150 nM; Applied potential ($E_{ap}$)=−0.15 V. The arrow shows the moment of the addition of $H_2O_2$.

Figure 3:
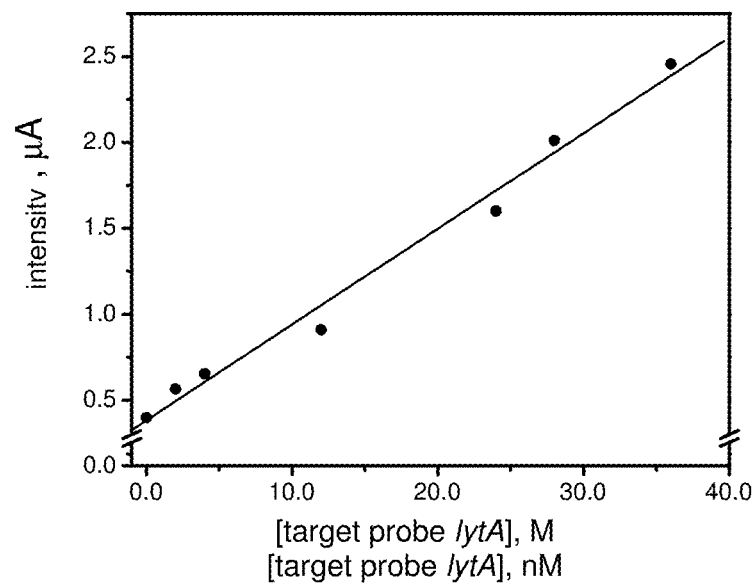

FIG. 3 Shows the calibration curve obtained for the amperometric determination of the target probe in the optimized experimental conditions.

Supporting electrolyte used, PBS (pH 7.4.) Experimental conditions: [immobilized probe]=1 µM; $E_{ap}$=−0.15 V.

Figure 4:
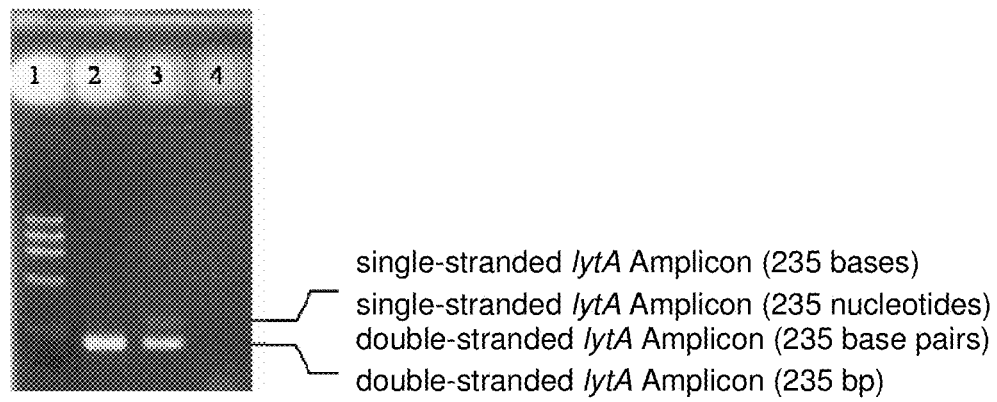

FIG. 4 Shows the agarose gel electrophoresis (1.5%.)

Lanes: 1) Replicative form markers of the DNA of φX174 digested with HaeIII, 2) conventional PCR and 3) aPCR using genomic DNA of the IR6 strain of S. pneumoniae as template, 4) control without DNA.

Figure 5:
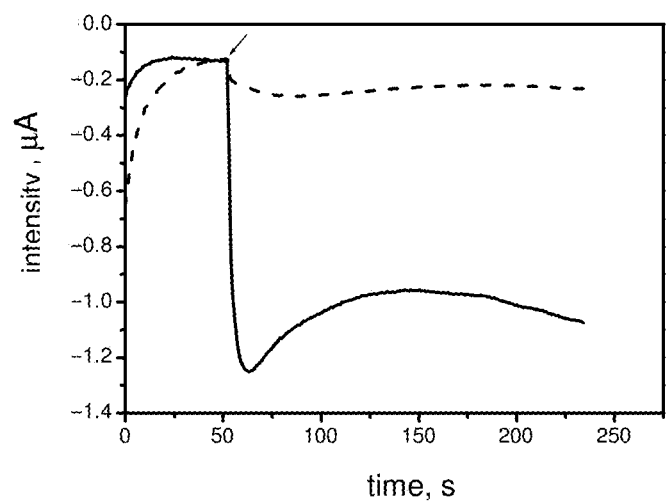

FIG. 5 Shows the amperograms obtained on the screen-printed electrodes modified by superparamagnetic particles (MBs) for a concentration of 2 nM of the amplicon obtained using genomic DNA of the IR6 strain of S. pneumoniae (–) as template.

Genomic DNA template of the IR6 strain of S. pneumoniae (–.)

The control sample ( - - - ) was amplified in absence of DNA.

Experimental conditions as in FIG. 3

The arrow shows the moment of the addition of $H_2O_2$.

Figure 6:
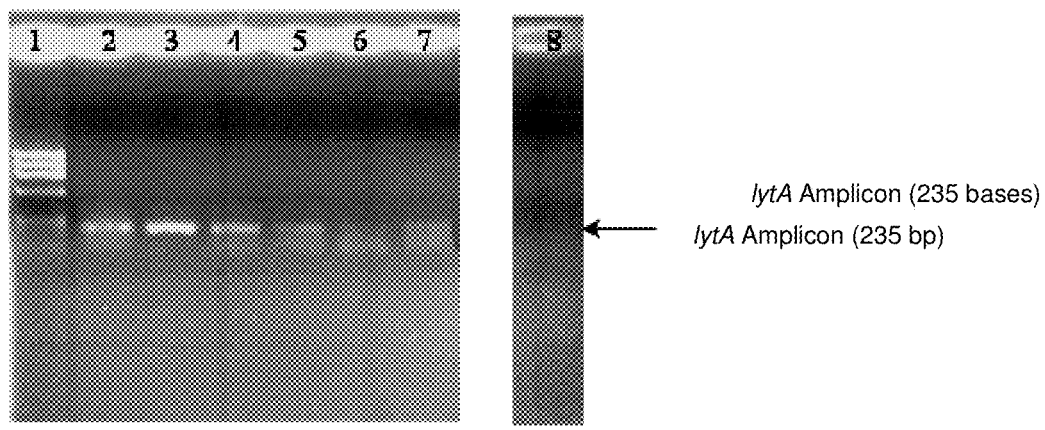

FIG. 6 Shows an agarose gel electrophoresis (1.5%) showing the aDPCR amplification products from the cell cultures of the R6 strain of S. pneumoniae.

Lanes: 1) Markers, RF DNA of φX174 digested with HaeIII.

2-7) aDPCRs from the cell culture of the R6 strain of S. pneumoniae with different cell density (in cfu ml$^{-1}$): $1.3 \times 10^7$ (2), $1.3 \times 10^6$ (3), $1.3 \times 10^5$ (4), $1.3 \times 10^4$ (5), $1.3 \times 10^3$ (6), $1.3 \times 10^2$ (7); lane 8, control without DNA.

Figure 7:
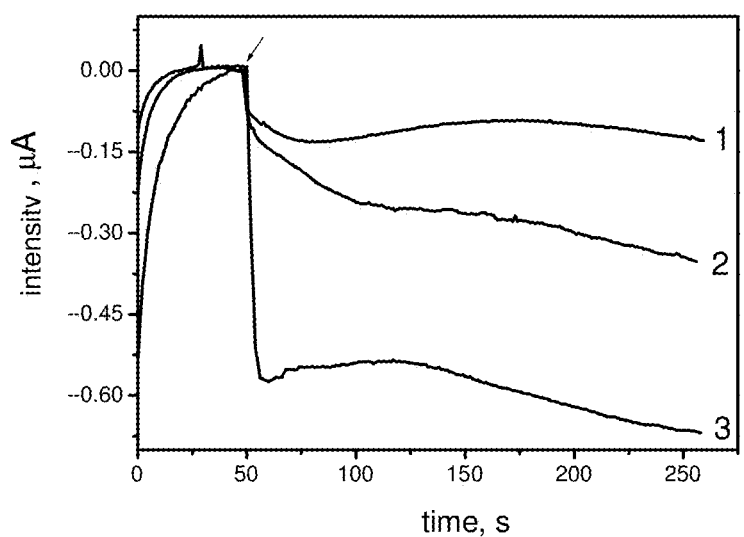

FIG. 7 Shows amperograms obtained on the screen-printed electrodes modified with the MBs for the aDPCR amplicons obtained.

1) Sample without DNA.
2) Cultures of the R6 strain of S. pneumoniae containing 130 cfu ml$^{-1}$,
3) Cultures of the R6 strain of S. pneumoniae containing $1.3 \times 10^7$ cfu ml$^{-1}$, Other experimental conditions are the same as in FIG. 3

The arrow shows the moment of the addition of $H_2O_2$.

Figure 8:
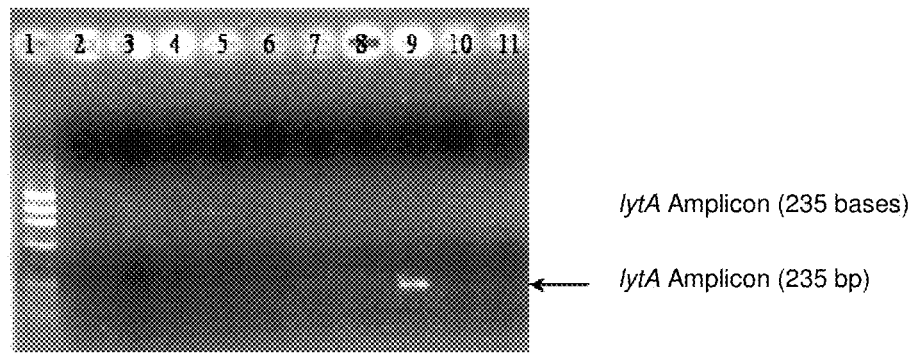

FIG. 8 Shows an agarose gel electrophoresis (1.5%) showing the aDPCR amplification products from the cell cultures of the R6 strain of S. pneumoniae and other bacteria.

Lanes: 1) Markers, RF DNA of φX174 digested with HaeIII.

aDPCRs of cell cultures (in cfu ml$^{-1}$) of: 2) S. oralis ($1.0 \times 10^8$); 3) S. sanguinis ($1.3 \times 10^8$); 4) S. pseudopneumoniae ($2.3 \times 10^8$); 5) S. mitis ($1.0 \times 10^8$); 6) S. constellatus ($1.4 \times 10^8$); 7) S. anginosus ($1.2 \times 10^8$); 8) S. mitis SK137 ($1.0 \times 10^8$); 9) S. pneumoniae R6 ($1.1 \times 10^8$); 10) E. coli ($7.5 \times 10^1$); 11) control without DNA.

Figure 9:
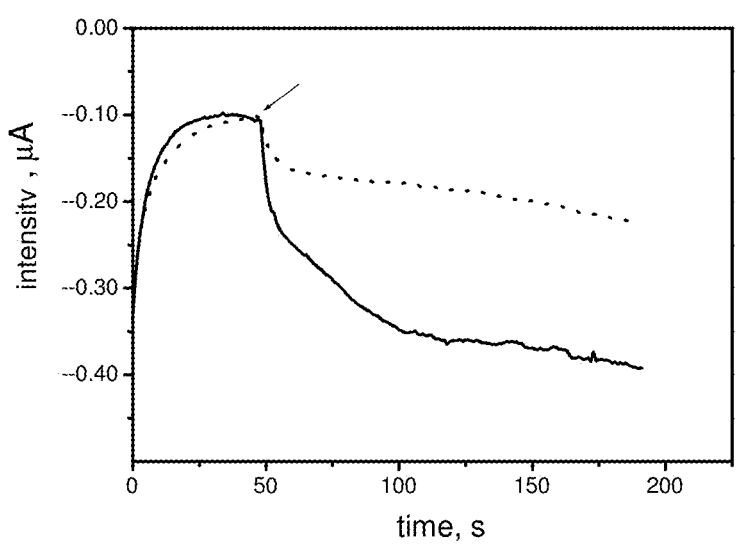

FIG. 9 Shows amperograms obtained on the screen-printed electrodes modified with the MBs for the amplification products.

1) Amperogram of the amplification products obtained using as aDPCR template cell cultures of S. mitis ($1.0 \times 10^8$ cfu ml$^{-1}$)
2) Amperogram of the amplification products obtained using as aDPCR template cell cultures of the R6 strain of S. pneumoniae (130 cfu ml$^{-1}$.)

Experimental conditions are the same as in FIG. 3

The arrow shows the moment of the addition of $H_2O_2$.

Figure 10:
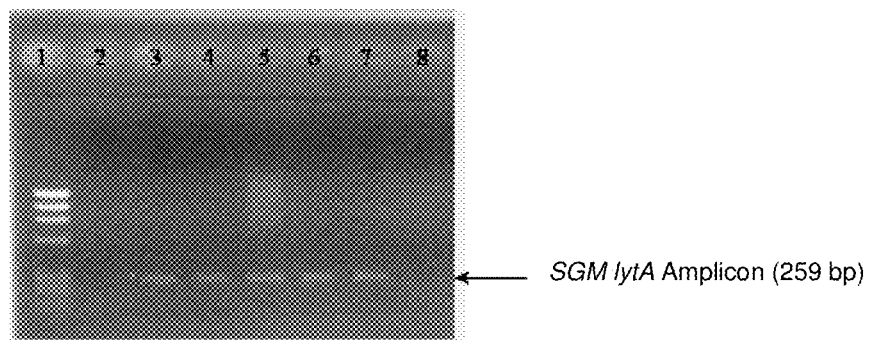

FIG. 10 Shows an agarose gel electrophoresis (1.5%) showing the aPCR amplification products from the cell cultures of the R6 strain of S. pneumoniae and other phylogenetically related species.

Lanes: 1) Markers, RF DNA of φX174 digested with HaeIII.

2 to 7) aPCRs using as template 100 ng of genomic DNA of the R6 strains of S. pneumoniae, CCUG 44455$^T$ of S. pseudopneumoniae, 10546, 1338, 1078 and 1629 respectively (the last 5 corresponding to SGM.)

8) Control without DNA.

EXAMPLES

The following assays, performed by the inventors, which describe the detection and/or quantification of *Streptococcus pneumoniae* (*S. pneumoniae*), illustrate the invention in a non-limiting way.

Example 1

Assays for the Detection of *S. pneumoniae*

1.1 Development of Disposable Magneto-Electrochemical Sensors.

Said magneto-electrochemical sensors are based on an enzyme amplification strategy and the use of superparamagnetic particles (MBs) MBs for the detection of a characteristic region of DNA of 235 base pairs (bp) of the lytA gene, specific of *S. pneumoniae*. For the election of this amplicon, an analysis was made of all sequences of the different alleles of lytA of all pneumococcal strains which sequence is known, including those of the 150 pneumococcal clinical isolates of *S. pneumoniae* sequenced by the inventors (see Table 2).

The chosen amplicon was centered in the 5' region of the lytA gene in a pneumococcal-specific zone (SEQ ID NO: 5.) Using the same specificity criterion for the SGM alleles, another zone of the 5' region of the lytA gene was chosen which was fully conserved between said bacteria and which showed differences with the alleles of the pneumococcal strains, where an amplicon of 259 by specific to the SGM was chosen (SEQ ID NO: 10).

Commercial MBs labeled with streptavidin were modified with a biotinylated DNA capture probe and were exposed to the biotinylated DNA amplicon which was obtained when using both a PCR or aPCR, using to that end genomic DNA of *S. pneumoniae* as template, and an asymmetric direct PCR (aDPCR) from bacterial cultures, in both cases using oligonucleotides (primers) allowing the specific amplification of the aforementioned gene region.

The enzymatic labeling of the resulting biotinylated hybrid was made through incubation with a commercial ultrasensitive streptavidin-peroxidase polymer, prepared through the covalent binding of streptavidin and HRP and a hydrophilic polymer backbone. The existence of multiple active biomolecules in each polymer chain increased the capacity to bind to biotinylated molecules, thus increasing the enzymatic charge and the amperometric signal due to the peroxidase, enabling a more sensitive detection than with conventional streptavidin-HRP conjugates.

After the enzymatic labeling of the hybrid DNA and immobilizing the resulting MB in gold-printed electrodes (modified with the redox mediator tetrathiafulvalene (TTF)), the detection of the DNA hybridization process was performed by amperometry using the appropriate substrate. The added hydrogen peroxide is reduced in the presence of HRP, and the regeneration of the reduced form of the enzyme is mediated by TTF. The $TTF^+$ generated is electrochemically reduced when the potential applied is more negative than the formal potential of the redox $TTF/TTF^+$ pair (Campuzano et al., 2005. Talanta, 66: 1310-1319).

With this procedure, up to 30 sensors a day can be manipulated (or more if the process is automated), showing the use of the methodology for the rapid, simple, specific, quantitative and ultrasensitive detection and identification (detection limit [LOD]=1.1 nM) of the DNA amplicons obtained by aPCR. Also, the DNA amplicons obtained from bacterial cultures are detected specifically when applying aDPCR, that is, without any need for prior extraction/purification of the genetic material.

The detection limit obtained, without prior concentration stages, was 100 cfu of *S. pneumoniae* per ml of sample, showing the great sensitivity of the genosensors developed as devices with relevant usefulness in the analysis of clinical samples. In the selected experimental conditions, the presence of other SGM (*S. oralis, Streptococcus sanguinis, S. pseudopneumoniae, S. mitis, Streptococcus constellatus* and *Streptococcus anginosus*) did not interfere in the detection and identification of *S. pneumoniae*.

1.2 Assay Reliability Verification.

The reliability of the proposed assay was verified comparing the reduction signal obtained for $H_2O_2$ after completing the biotinylated probe hybridization process in the presence and absence of the complementary synthetic sequence labeled with biotin and using TTF as mediator. The immobilized TTF on the electrode surface mediates the catalytic reduction of $H_2O_2$ produced by the HRP enzyme. Thus, the electrochemical reduction of the $TTF^*$ generated can be measured at a determined potential. The signal obtained is directly proportional to the amount of target oligonucleotide used. As shown in FIG. 2, when the process is made in the absence of the biotinylated target probe, an insignificant amperometric response is observed when adding $H_2O_2$ to the surface of the modified electrode, verifying that the signal obtained after the hybridization is significantly higher, showing the greatest immobilization of the enzymatic marker in the hybridized DNA. The results obtained show that the proposed assay is appropriate for the electrochemical detection of the hybridization processes of the target probe that characterizes the lytA alleles of pneumococcal strains.

The same protocol has been used to research the specificity of the hybridization process making said process with non-complementary sequences and single-base mismatch sequences (0.1 μM≡10 pmol.) While an insignificant amperometric signal is observed after the hybridization with the non-complementary oligonucleotide (similar to the signal obtained in the absence of the biotinylated target probe), after making the hybridization process with single-base mismatch sequences an amperometric response similar to the one observed with target probes (perfectly complementary) is observed. These results show that the methodology developed can be used to distinguish between complementary sequences and non-complementary sequences, but that more restrictive hybridization conditions should be optimized in order to discriminate single-base mismatches.

1.3 Detection of Complementary Synthetic Oligonucleotides.

Using the aforementioned optimized experimental conditions, the corresponding calibration has been constructed for the biotinylated target probe that characterize pneumococcal lytA alleles (FIG. 3.) Table 1 shows the results obtained.

TABLE 1

Characteristics of the amperometric determination method with enzymatic amplification for lytA alleles of *S. pneumoniae*.

| Characteristic | Value |
| --- | --- |
| Lineal Interval (nM) | 5-36 (3-23 ng) |
| Slope (A $M^{-1}$) | 56 ± 3 |
| Correlation Coefficient | 0.993 |
| Detection Limit (nM) | 5.1 |
| RSD* (n = 8) (%) | 8.7 |

*RSD, Relative Standard Deviation.

Detection limits (dl) and determination limits (dtl) were calculated according to the criteria $dl=3s_B \, m^{-1}$ (16) and $dtl=10s_B \, m^{-1}$ (Long y Winefordner, 1983. Anal. Chem., 55: 712A-724A), respectively, where m is the slope of the calibration curve and $s_B$ corresponds to the standard deviation (n=10) of the amperometric signals obtained to a target probe concentration of 2.0 nM. The dl obtained represents an acceptable sensitivity, taking into account that at this point PCR amplification has not been used yet.

Since the genosensors based on disposable screen-printed electrodes require the use of a new electrode for each measurement, the reproducibility of the analytical signals obtained with different genosensors made in the same way is an essential aspect to evaluate in order to guarantee the real practical usefulness of this design. To evaluate this aspect, the current intensity values obtained were compared with 8 genosensors (using 13 nmoles≅8.5 ng of biotinylated target oligonucleotide), prepared from different batches of modified particles. From the values obtained we have an RSD of 8.7%, which secures that the manufacturing process of the genosensors is very reproducible and reliable.

1.4. Detection of DNA Amplicons Obtained through aPCR.

Recently, different protocols have been proposed to optimize DNA detection by means of the amplification through PCR, including aPCR and direct PCR (DPCR), which allows the amplification and detection of specific sequences of nucleic acids without needing any prior extraction of genetic material of the cells. The use of aPCR leads to a greater sensitivity than symmetric PCR due to the presence of single-stranded fragments in great proportion, which can non-competitively hybridize with the probe (Poddar, 2000. Mol. Cell. Probes, 14: 25-32.) This also implies a faster hybridization of the amplicons in the developed genosensor.

In order to increase the sensitivity of the method developed, it was decided to apply the proposed format to the detection of amplicon resulting from the aPCR, a DNA fragment of 235 bases that contain the complementary sequence of the immobilized capture probe in the MBs. The products obtained were confirmed through electrophoresis in agarose gels using ethidium bromide as developer. As it can be seen (FIG. 4), unlike what happens with a normal PCR (in which the whole amplicon generated is double stranded), with aPCR there appear 2 bands in the electrophoresis gel. Since double-stranded DNA migrates faster than single-stranded DNA (Gunnarsson et al., 2006. Nat. Protoc., 1: 3011-3018), the band with less electrophoretic mobility observed corresponds to the single-stranded fragment and the one with greater mobility corresponds to double-stranded DNA (Kai et al., 1998. Biotechnol. Techniques, 12: 935-939.) The electrophoretic results confirm the amplification of the PCR products with the correct size (235 by or nucleotides), in spite of the low efficiency of the ethidium bromide stain for the single-stranded DNA.

The samples obtained through aPCR were purified and diluted adequately (100-1000 times in Tris-HCl buffer pH 7.2) and they were directly used for the electrochemical detection. As it can be seen in FIG. 5, the control used as target in the aPCR (without genomic DNA), does not produce a significant amperometric signal. This confirms again the absence of unspecific adsorptions from the enzymatic polymer in the absence of hybridization. FIG. 5 also shows that the presence of the amplicon at a concentration of 2 nM gives place to a noticeable amperometric signal.

When studying the dependency of the amperometric signal with the concentration of the amplicon obtained from S. pneumoniae R6, a lineal interval was obtained for the quantification of the amplicon, obtained through aPCR between 1.0 and 6.0 nM, giving place to a sensitivity of 134±6 A $M^{-1}$ (≅2.4 times more than the sensitivity obtained for the detection of the target probe) (Table 1) and a correlation coefficient of 0.997. A reduction in the sensitivity was observed for high concentrations of amplicon, which can be due to the threading of the long chains of DNA which makes the efficiency of the hybridization process difficult. The detection and determination limits were calculated according to the same criteria mentioned above and taking as SD the standard deviation (n=10) for the amperometric signals obtained at a concentration level of 1.0 nM of amplicon via aPCR, obtaining values of 1.1 and 3.7 nM, respectively. A RSD value of 6.9% was obtained for 7 measurements of a solution with an amplicon concentration of 1.1 nM obtained through aPCR. This result can be considered excellent if we take into account the low concentration of amplicon and the type of device (single-use genosensor) used.

1.5. Detection of Pneumococcus through aDPCR.

As it was mentioned before, DPCR enables to amplify and detect specific amino acid sequences without any need to previously extract the genetic material of the cells. Due to its fast speed, simplicity and little manipulation of the sample, the DPCR has proved to be useful in the detection and quantification of bacteria in environmental samples (Fode-Vaughan et al., 2001. Biotechniques, 31: 598-607.) In this technique, the factor determining the amount of DNA available is the efficiency of the cellular permeabilization, which can be increased using cellular membrane permeabilization methods in order to allow the entrance of reagents for the amplification and to delay the diffusion of the products outside the cells, also avoiding the destruction of its morphology and of the microstructure of the microbial community (Hodson et al., 1995. Appl. Environ. Microbiol., 61: 4074-4082.)

In order to improve the sensitivity and reduce the assay time, the methodology developed was applied to the detection of the amplicons obtained through aDPCR made directly on cell cultures of pneumococcus. Following the procedure described biotinylated amplicons of 235 by (or nucleotides) were obtained directly from cultures of S. pneumoniae R6 with different cell density. FIG. 6 shows the products of aDPCR using cultures of the R6 strain of S. pneumoniae with different cell density. As it can be observed, amplicon was obtained with only 100 cfu $ml^{-1}$ of culture.

The samples obtained from the aDPCR from cell cultures with concentrations between 130 and $1.3 \times 10^7$ cfu $ml^{-1}$ were diluted 1:200 using a Tris-HCl buffer pH 7.2 and aliquots of 100 µl were used prepared as analyte to prepare the genosensors. As it can be seen in FIG. 7 (amperogram 1), almost no amperometric signal is obtained for negative control, confirming again the absence of unspecific absorption of the enzymatic marker in the absence of DNA hybrid formation. Amperograms 2 and 3 of the same figure show the signals obtained for the amplicons obtained through aDPCR from the cultures of the R6 strain of S. pneumoniae with different cell density. As it can be seen, the amperometric signal obtained increases the culture concentration. This result is logic taking into account that, in the amplification conditions selected, the final concentration of the amplicon obtained depends on that of the culture used as template in the aDPCR, as it can be seen in FIG. 6 and as it can be deduced from the results given by the spectrophotometric measurements of the concentration of the purified amplicons (30.3-12.3 ng/µl.) These results have been confirmed after five series of measurements.

The results described show that the method developed, besides allowing a simple discrimination between 100 cfu $ml^{-1}$ of pneumococcus culture and the control, allow an approximate quantification of the levels of this bacterium using aDPCR, clearly showing the applicability of disposable magnetic genosensors combined with the aDPCR to evaluate the presence of absence of pneumococcus in clinical samples.

1.6 Selectivity of the Methodology Developed.

The selectivity of the methodology developed was assayed using several SGM, as well as other bacteria as phylogenetically far-related from pneumococcus as *E. coli*. As it can be seen in FIG. 8, when aDPCR is used, from all the assayed strains only the amplicon corresponding to *S. pneumoniae* was obtained, which shows the high specificity of the methodology developed in the selected experimental conditions of amplification.

At this point, it is worth noticing that when aDPCR is made on stocks of three capsulated strains of *S. pneumoniae* (TIGR4, D39 and Dawn), kept in glycerol at −80° C., the expected amplicon is also obtained, which shows the usefulness of the methodology for the detection of both capsulated and non-capsulated pneumococcus.

FIG. 9 shows the resulting amperograms for the amplicons obtained using as template of the aDPCR a culture of *S. pneumoniae* of 130 cfu ml$^{-1}$ and a culture of *S. mitis* of $1.0 \times 10^8$ cfu ml$^{-1}$ showing the selective detection of *S. pneumoniae* concentrations, approximately $10^6$ times lower than that of *S. mitis*.

1.7. Application to Samples of Inoculated Biological Fluids.

Although the developed methodology applicability to the detection of pneumococcus in different clinical samples (blood, cerebrospinal fluid, etc.) is to be thoroughly evaluated in the future, preliminary assays have been made making aDPCR on ram defibrinated blood samples, human saliva and urine inoculated with pneumococcus which proved to be promising, obtaining amplicon using as template 2 µl of sample (inoculated with $1.0 \times 10^4$ cfu ml$^{-1}$ of pneumococcus) without any need to apply any prior treatment thereto.

1.8. Development of a Similar Methodology for the Selective Detection and Quantification of Other Streptococci of the Mitis Group (SGM).

Due to the interest in the unequivocal identification of the streptococcus responsible for an infectious process, a complementary methodology was developed which, using another appropriate capture probe and making the amplification with another pair of oligonucleotides, allows the selective detection of lytA alleles that characterize SGM.

The selectivity of this alternative methodology was evaluated making aPCR with genomic DNA and aDPCR of SGM cultures using both DNA and cells of *S. pneumoniae* R6 as negative control. As it can be seen in FIG. 10, the new selected pair of primers enables to obtain the corresponding amplicon (in this case of 259 by or nucleotides) and, therefore, the specific detection of the strains that carry the alleles that characterize SGM.

At this point, it is worth noticing that, so far, there is no commercially available methodology that enables to discriminate lytA alleles of pneumococcus and SGM strains and, therefore, to distinguish between pneumococcus and other phylogenetically closely related streptococci which can also be important pathogens, especially in immunocompromised patients.

Materials and Methods

1. Devices and Electrodes Used.

The amperometric measurements were made using an Eco Chemie Autolab PSTAT 10 Potentiostat equipped with the EDC module and controlled by the GPES 4.9 (General Purpose Electrochemical System) software.

The electrochemical measurements were made using screen-printed electrodes with gold paste cured at high temperature 220AT (Dropsens) (3.4×1.0×0.05 cm), SPGEs AT.

A MB concentrator (Dynal MPC-S, Dynal Biotech ASA) was used to modify the MBs.

All the PCR experiments were made in an Applied Biosystems 2720 thermal cycler.

2. Strains, Reagents and Solutions Used.

To prepare all the solutions used, we used deionized water obtained using a Millipore Milli-Q system.

All reagents and solvents used were high-quality ones for analysis.

B&W buffer: 10 mM Tris-HCl, pH 7.5, 1 mM EDTA, 2.0 M NaCl.

Tetrathiafulvalene, TTF (Aldrich.)

Ultrasensitive streptavidin-horseradish peroxidase polymer (HRP) (Sigma.)

MBs modified with streptavidin (Dynabeads M-280 streptavidin, 10 mg ml$^{-1}$) (lnvitrogen Dynal AS.)

Luria Bertani (LB) medium (Scharlau.)

C+Y medium: C medium (Lacks y Hotchkiss, 1960. Biochim. Biophys. Acta, 39: 508-597) supplemented with yeast extract 0.08%.

TE buffer (pH 8.0): 10 mM Tris-HCl containing 1 mM of EDTA.

Tris-HCl buffer (pH 7.2): 50 mM of Tris-HCl containing 20 mM of NaCl.

PBS buffer: 10 mM Sodium Phosphate Buffer (pH 7.4) containing 138 mM of NaCl and 2.7 mM of KCl.

PBST buffer: PBS solution (pH 7.4) containing 0.05% (v/v) of Tween 20.

Solution of TTF 0.5 M: Prepared dissolving 5.1 mg of the compound in 50 µl of acetone.

Dissolution pattern of $H_2O_2$ 0.1 M: 10 µl of the commercial solution at 30% (v/v) are dissolved in 1 ml of the regulatory solution of PBS (pH 7.4.) The solutions with less concentration are prepared diluting the appropriate volume of the prior solution with the same buffer solution.

Dissolution of the streptavidin-HPR polymer 10 µg ml$^{-1}$: 10 µl of the original solution (1.0 mg ml$^{-1}$) are diluted in 1 ml of PBST (pH 7.4.)

Oligonucleotides (Sigma)

For the specific detection of lytA alleles of *S. pneumoniae* the following synthetic oligonucleotides were used:

Biotinylated capture probe (CSP lytA) at the 5' end (SEQ ID NO: 1.)

Biotinylated target probe (TSP lytA) at the 5' end (SEQ ID NO: 2.)

Direct primer (FSP_lytA) (SEQ ID NO: 3.)

Reverse primer (RSP_lytA) biotinylated at the 5' end (SEQ ID NO: 4.)

lytA$_{R6}$ (amplicon of *S. pneumoniae*, 235 bp, direction 5'→3'): SEQ ID NO: 5 The hybridized biotinylated probe with the nucleotide sequence 187 to 206, assigning position 1 to the first nucleotide of the initiation codon of the lytA gene.

To design said probes and primers it was necessary to have the sequence of the lytA gene of 115 isolates as shown in Table 2.

TABLE 2

New sequences (not published or included in public data bases) of the lytA gene obtained from 115 clinical isolates of *S. pneumoniae*.

| STRAIN | ISOLATION YEAR | SEROTYPE | ORIGIN[a] | ALLELE | SEQUENCES |
|---|---|---|---|---|---|
| 1001 | 1989 | 3 | CSF | A | SEQ ID NO: 11 |
| 1990 | 1991 | 3 | BLOOD | A | SEQ ID NO: 11 |
| 1998 | 1991 | 3 | CSF | E | SEQ ID NO: 15 |
| 2629 | 1993 | 3 | CSF | A | SEQ ID NO: 11 |
| 2778 | 1993 | 3 | BLOOD | A | SEQ ID NO: 11 |
| 2812 | 1993 | 3 | BLOOD | A | SEQ ID NO: 11 |
| 3003 | 1994 | 3 | BLOOD | B | SEQ ID NO: 12 |
| 3086 | 1994 | 3 | BLOOD | B | SEQ ID NO: 12 |

TABLE 2-continued

New sequences (not published or included in public data bases) of the lytA gene obtained from 115 clinical isolates of S. pneumoniae.

| STRAIN | ISOLATION YEAR | SEROTYPE | ORIGIN[a] | ALLELE | SEQUENCES |
|---|---|---|---|---|---|
| 3227 | 1994 | 3 | PLEURAL F. | A | SEQ ID NO: 11 |
| 3404 | 1995 | 1 | BLOOD | F | SEQ ID NO: 16 |
| 3474 | 1995 | 1 | BLOOD | F | SEQ ID NO: 16 |
| 3533 | 1995 | 1 | PLEURAL F. | F | SEQ ID NO: 16 |
| 4033 | 1996 | 1 | BLOOD | F | SEQ ID NO: 16 |
| 4066 | 1996 | 3 | CSF | B | SEQ ID NO: 12 |
| 4107 | 1997 | 3 | BLOOD | A | SEQ ID NO: 11 |
| 4520 | 1998 | 3 | BLOOD | A | SEQ ID NO: 11 |
| 4532 | 1998 | 3 | BLOOD | B | SEQ ID NO: 12 |
| 4889 | 1998 | 3 | BLOOD | A | SEQ ID NO: 11 |
| 4920 | 1999 | 3 | BLOOD | A | SEQ ID NO: 11 |
| 5294 | 1999 | 1 | PLEURAL F. | F | SEQ ID NO: 16 |
| 5407 | 2000 | 3 | SPUTUM | A | SEQ ID NO: 11 |
| 5410 | 2000 | 3 | SPUTUM | B | SEQ ID NO: 12 |
| 5416 | 2000 | 3 | BLOOD | A | SEQ ID NO: 11 |
| 5456 | 2000 | 1 | BLOOD | F | SEQ ID NO: 16 |
| 5788 | 2000 | 3 | CSF | A | SEQ ID NO: 11 |
| 5796 | 2000 | 1 | BLOOD | F | SEQ ID NO: 16 |
| 5814 | 2001 | 3 | SPUTUM | B | SEQ ID NO: 12 |
| 6008 | 2001 | 1 | PLEURAL F. | F | SEQ ID NO: 16 |
| 6202 | 2002 | 3 | SPUTUM | B | SEQ ID NO: 12 |
| 6316 | 2002 | 3 | SPUTUM | B | SEQ ID NO: 12 |
| 6330 | 2002 | 1 | BLOOD | F | SEQ ID NO: 16 |
| 6411 | 2002 | 3 | BLOOD | B | SEQ ID NO: 12 |
| 6441 | 2002 | 1 | BLOOD | F | SEQ ID NO: 16 |
| 6497 | 2002 | 1 | BLOOD | F | SEQ ID NO: 16 |
| 6549 | 2002 | 3 | SPUTUM | B | SEQ ID NO: 12 |
| 6612 | 2003 | 3 | PLEURAL F. | A | SEQ ID NO: 11 |
| 6729 | 2003 | 1 | BLOOD | F | SEQ ID NO: 16 |
| 6746 | 2003 | 1 | PLEURAL F. | F | SEQ ID NO: 16 |
| 6810 | 2003 | 1 | BLOOD | F | SEQ ID NO: 16 |
| 6817 | 2003 | 1 | BLOOD | F | SEQ ID NO: 16 |
| 6952 | 2003 | 3 | PLEURAL F. | A | SEQ ID NO: 11 |
| 6979 | 2003 | 3 | BLOOD | B | SEQ ID NO: 12 |
| 6987 | 2003 | 3 | BLOOD | A | SEQ ID NO: 11 |
| 6993 | 2003 | 1 | BLOOD | F | SEQ ID NO: 16 |
| 7027 | 2004 | 1 | BLOOD | F | SEQ ID NO: 16 |
| 7132 | 2004 | 3 | PLEURAL F. | A | SEQ ID NO: 11 |
| 7151 | 2004 | 3 | BLOOD | B | SEQ ID NO: 12 |
| 7207 | 2004 | 3 | BLOOD | A | SEQ ID NO: 11 |
| 7212 | 2004 | 1 | PLEURAL F. | F | SEQ ID NO: 16 |
| 7225 | 2004 | 3 | BLOOD | A | SEQ ID NO: 11 |
| 7300 | 2004 | 3 | BLOOD | A | SEQ ID NO: 11 |
| 7312 | 2004 | 3 | SPUTUM | B | SEQ ID NO: 12 |
| 7345 | 2004 | 1 | BLOOD | F | SEQ ID NO: 16 |
| 7361 | 2004 | 1 | BLOOD | F | SEQ ID NO: 16 |
| 7377 | 2004 | 3 | SPUTUM | A | SEQ ID NO: 11 |
| 7374 | 2004 | 3 | BLOOD | B | SEQ ID NO: 12 |
| 7386 | 2004 | 3 | PLEURAL F. | A | SEQ ID NO: 11 |
| 7410 | 2005 | 1 | BLOOD | F | SEQ ID NO: 16 |
| 7498 | 2005 | 1 | BLOOD | F | SEQ ID NO: 16 |
| 7518 | 2005 | 1 | BLOOD | F | SEQ ID NO: 16 |
| 7536 | 2005 | 1 | BLOOD | F | SEQ ID NO: 16 |
| 7542 | 2005 | 3 | PLEURAL F. | B | SEQ ID NO: 12 |
| 7557 | 2005 | 1 | BLOOD | F | SEQ ID NO: 16 |
| 7558 | 2005 | 1 | BLOOD | F | SEQ ID NO: 16 |
| 7629 | 2005 | 1 | BLOOD | F | SEQ ID NO: 16 |
| 7655 | 2005 | 1 | BLOOD | F | SEQ ID NO: 16 |
| 7715 | 2005 | 3 | BLOOD | A | SEQ ID NO: 11 |
| 7827 | 2005 | 3 | BLOOD | A | SEQ ID NO: 11 |
| 7840 | 2005 | 1 | BLOOD | F | SEQ ID NO: 16 |
| 7845 | 2005 | 3 | BLOOD | A | SEQ ID NO: 11 |
| 2900 | 2006 | 3 | SPUTUM | A | SEQ ID NO: 11 |
| 8056 | 2006 | 1 | PLEURAL F. | F | SEQ ID NO: 16 |
| 8057 | 2006 | 3 | PLEURAL F. | B | SEQ ID NO: 12 |
| 8061 | 2006 | 1 | BLOOD | F | SEQ ID NO: 16 |
| 8069 | 2006 | 1 | BLOOD | D | SEQ ID NO: 14 |
| 8080 | 2006 | 1 | BLOOD | F | SEQ ID NO: 16 |
| 8084 | 2006 | 1 | SPUTUM | F | SEQ ID NO: 16 |
| 8120 | 2006 | 1 | BLOOD | F | SEQ ID NO: 16 |
| 8150 | 2006 | 3 | ABSCESS | B | SEQ ID NO: 12 |
| 8173 | 2006 | 3 | BLOOD | A | SEQ ID NO: 11 |
| 8199 | 2006 | 3 | PLEURAL F. | B | SEQ ID NO: 12 |
| 8205 | 2006 | 3 | BLOOD | A | SEQ ID NO: 11 |
| 8230 | 2006 | 1 | BLOOD | F | SEQ ID NO: 16 |
| 8237 | 2006 | 3 | SPUTUM | B | SEQ ID NO: 12 |
| 8240 | 2006 | 3 | BLOOD | A | SEQ ID NO: 11 |
| 8273 | 2006 | 1 | SPUTUM | F | SEQ ID NO: 16 |
| 8278 | 2006 | 3 | CSF | A | SEQ ID NO: 11 |
| 8284 | 2006 | 1 | BLOOD | F | SEQ ID NO: 16 |
| 8295 | 2006 | 3 | BLOOD | C | SEQ ID NO: 13 |
| 8328 | 2006 | 3 | BLOOD | B | SEQ ID NO: 12 |
| 8344 | 2006 | 1 | BLOOD | F | SEQ ID NO: 16 |
| 8359 | 2006 | 1 | PLEURAL F. | F | SEQ ID NO: 16 |
| 8368 | 2007 | 3 | SPUTUM | B | SEQ ID NO: 12 |
| 8417 | 2007 | 1 | PLEURAL F. | F | SEQ ID NO: 16 |
| 8431 | 2007 | 1 | BLOOD | F | SEQ ID NO: 16 |
| 8446 | 2007 | 1 | BLOOD | F | SEQ ID NO: 16 |
| 8516 | 2007 | 1 | PLEURAL F. | F | SEQ ID NO: 16 |
| 8564 | 2007 | 3 | BLOOD | B | SEQ ID NO: 12 |
| 8573 | 2007 | 3 | SPUTUM | B | SEQ ID NO: 12 |
| 8653 | 2007 | 3 | BLOOD | A | SEQ ID NO: 11 |
| 8715 | 2007 | 1 | BLOOD | F | SEQ ID NO: 16 |
| 8797 | 2007 | 3 | PLEURAL F. | B | SEQ ID NO: 12 |
| 8874 | 2007 | 1 | BLOOD | F | SEQ ID NO: 16 |
| 8955 | 2008 | 3 | BLOOD | A | SEQ ID NO: 11 |
| 9042 | 2008 | 1 | CSF | F | SEQ ID NO: 16 |
| 9270 | 2008 | 1 | BLOOD | F | SEQ ID NO: 16 |
| 9322 | 2008 | 1 | BLOOD | F | SEQ ID NO: 16 |
| 9458 | 2008 | 1 | PLEURAL F. | F | SEQ ID NO: 16 |
| 9494 | 2009 | 1 | BLOOD | F | SEQ ID NO: 16 |
| 9509 | 2009 | 1 | PLEURAL F. | F | SEQ ID NO: 16 |
| 9521 | 2009 | 1 | CSF | F | SEQ ID NO: 16 |
| 9522 | 2009 | 1 | BLOOD | F | SEQ ID NO: 16 |
| 9560 | 2009 | 1 | BLOOD | F | SEQ ID NO: 16 |
| 9572 | 2009 | 1 | PLEURAL F. | F | SEQ ID NO: 16 |
| 9638 | 2009 | 1 | BLOOD | F | SEQ ID NO: 16 |

[a]CSF, cerebrospinal fluid.

For the specific detection of lytA alleles of SGM, the following synthetic oligonucleotides were used:
Biotinylated capture probe (CSMG_lytA) at the 5' end (SEQ ID NO: 6.)
Biotinylated target probe (TSMG_lytA) at the 5' end (SEQ ID NO: 7.)
Direct primer (FSMG_lytA) (SEQ ID NO: 8.)
Reverse primer (RSMG_lytA) biotinylated at the 5' end (SEQ ID NO: 9.)
lytA$_{AJ252194}$ (amplicon of SGM, 259 bp, direction 5'→3'): SEQ ID NO: 10. The hybridized biotinylated probe with the nucleotide sequence 207 to 230.

For the experiments performed, the following bacterial species and strains were used: R6 strains (Hoskins et al., 2001. J. Bacteriol., 183: 5709-5717), TIGR4 (Tettelin et al., 2001. Science, 293: 498-506), D39 (Lanie et al., 2007. J. Bacteriol., 189:38-51) and Dawn (Llull et al., 2000. Microb. Drug. Resist., 6: 269-275) of *S. pneumoniae*, the standard strain of *S. pseudopneumoniae* CCUG 44455$^T$, *S. oralis* NCTC 11427$^T$, *S. sanguinis* CECT 480$^T$, *S. constellatus* NCTC 10708, *S. anginosus* K51-Y, *S. agalactiae* CECT 183$^T$, *S. gordonii* CECT 804$^T$, *S. iniae* CECT 7363$^T$, *S. salivarius* CECT 805$^T$, the strains NCTC 12261$^T$, SK137 (3), SK598 (4), B6 y HER 1055 (Romero et al., 2004. J. Bacteriol., 186: 8229-8239) of *S. mitis* and the strains 1078/1997, 1338/1996, 1629/1997, 101/1987, 1230/1996, 782/1996, 11923/1992 and 10546/1994 that correspond to the SGM (Llull et al., 2006. J. Clin. Microbiol., 44: 1250-1256.) Also, as negative control, *E. coli* DH5α was used (Sambrook y Russell, 2001. Molecular Cloning. A Laboratory Manual. Cold Spring Harbor Laboratory Press, Cold Spring Harbor, N.Y.)

3. Bacterium Culture Methods.

The *E. coli* cultures were made in LB medium over night at 37° C. with constant stirring. Later, stocks were prepared in glycerol (10%, v/v), diluted in series, 100 µl of the corresponding dilutions are sown in Petri dishes containing LB medium and they are incubated for 24 hours at 37° C. to count the colonies. The culture of streptococci is made in C+Y medium at 37° C. without stirring. When the culture reaches a $DO_{550}$ of about 0.4, stocks are prepared in glycerol (10%) while serial dilutions are made which are sown (100 µl) in blood agar plates and incubated for 24 hours at 37° C. to count the colonies.

4. Preheating and Modification of the Indicator Electrodes.

Screen-printed gold electrodes curated at high temperature (Dropsens) are pretreated making ten consecutive cyclic sweeps with a potential of 0.00–+1.25 V, at a speed of 100 mV s–$^1$, in a solution 0.5 M of $H_2SO_4$ containing KCl 10 mM. 5 µl of a 0.5 M solution of TTF are deposited on the dry surface of the pretreated electrodes and they are left to dry at room temperature.

5. Modification of MBs and Amperometric Transduction.

For this procedure, 10 µl of the commercial suspension of MBs modified with streptavidin are placed in a 1.5 ml microcentrifugation tube and are washed with 10 µl of B&W buffer. The particles are placed in the MB concentrator and, after 2 minutes, the supernatant is extracted. This procedure is repeated twice. Next, 100 µl of a 1 µM 100 pmoles) solution of the capture probe of DNA (biotinylated at the 5'end and prepared in the B&W buffer) are added and incubated at 37° C. for 60 minutes in a stirrer at 600 rpm. Next, the particles are washed twice, using 100 µl of Tris-HCl buffer (pH 7.2) each time. Later, the desired amount of complementary DNA (labeled with biotin at the 5' end and prepared in the Tris-HCl buffer, pH 7.2) is added and incubated at 37° C. for 60 minutes in a stirrer at 600 rpm. The mixture is placed in the MB concentrator and, after 2 minutes, the supernatant is separated. Then, the particles modified with the hybrid are washed twice following the procedure above (Tris-HCl buffer pH 7.2.) Next, 100 µl of a streptavidin-HRP solution (10 µg ml$^{-1}$) prepared in PBST (pH 7.4) are added and left to react for 60 minutes at 37° C. stirring at 600 rpm. After the reaction time, the particles are washed five times for 5 minutes each time with 500 µl of PBST and one last time with PBS (pH 7.4.)

The MBs, once modified, are resuspended in 45 µl of PBS (pH 7.4) and immobilized on the surface of the screen-printed electrodes pretreated and modified with TTF. The particles are fixed to the electrode surface by placing a neodymium magnet under the working electrode.

The amperometric answers are obtained applying a potential of –0.15 V to the screen-printed electrodes with the modified particles deposited on the surface. When a stationary state is reached 5 µl of a 3.5 mM solution of $H_2O_2$ are added to the measurement potential.

Figure 1:
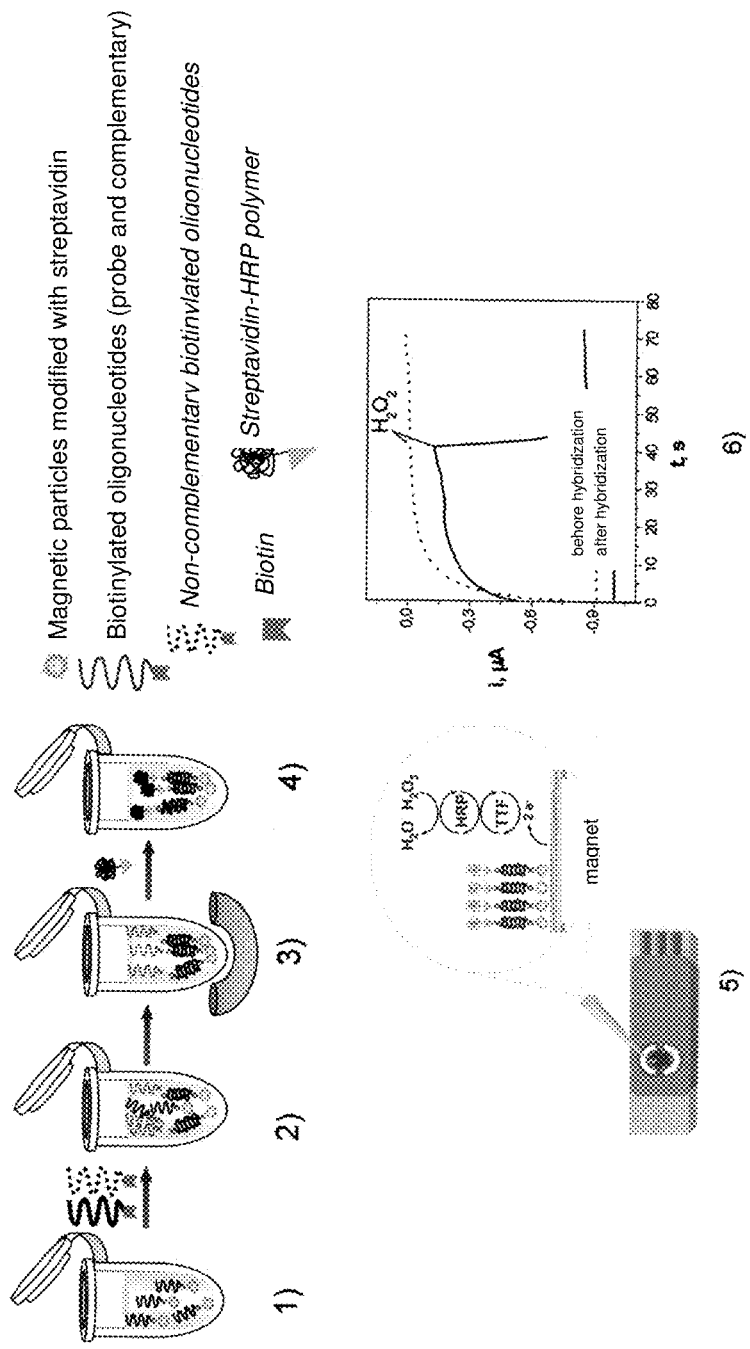
FIG. 1 Shows the electrode modification procedure and measurement based on the use of MBs and the enzyme amplification of the amperometric signal.

FIG. 1 schematically shows the procedure described herein. Briefly, the method consists of the capture of the biotinylated probe of 20 bases on the surface of the modified MBs with streptavidin and its later hybridization with a target probe or with the amplicon obtained through aPCR (or aDPCR.) The hybrid formed is labeled with an ultrasensitive streptavidin-peroxidase polymer and the modified MBs are deposited on the surface of an electrode modified with TTF. The use of MBs allows the immobilization of the DNA hybrids directly on the surface of the screen-printed electrodes avoiding unspecific adsorption associated to the immobilization processes on the surface of metallic electrodes. Finally, the hybridization process is amperometrically monitored at a potential of –0.15 V (vis-à-vis a Ag/AgCl) after adding a solution of $H_2O_2$.

6. Obtaining DNA Amplicon of 235 Bases of the lytA Gene using aPCR.

To carry out the amplification of the fragment of 235 bases of the lytA gene of *S. pneumoniae*, aPCR was used, a procedure that enables to amplify preferably a single strand of original DNA containing the complementary sequence (20-mer), to the immobilized synthetic probe on the MBs modified with streptavidin, thus being able to perform the direct detection of the hybridization process.

The aPCR was performed in a final volume of 100 µl of a mix containing, at least, 2 µl of the extract of genomic DNA of the R6 strain of *S. pneumoniae* (50 ng/µl), 1.6 µl of the solution of the direct primer (5 µM), 16 µl of the solution of the reverse biotinylated primer (5 µM) and other components following the standard protocol for the amplification using PCR with the Taq DNA polymerase. The aPCR conditions were: denaturalization (94° C., 4 min), followed by 35 cycles at 94° C. for 1 minute (denaturalization), 60° C. for 1 minute (annealing), 72° C. for 1 minute (extension) and 3 minutes of final extension.

When the limiting primer is consumed, the remaining primer, which is the reverse biotinylated primer, continues to amplify the fragment of DNA, thus the resulting product in the PCR is mainly a single-stranded chain of 235 bases biotinylated at the 5' end.

7. Obtaining the Amplicon of 235 Bases of the lytA Gene using aDPCR.

In this case, the R6 strain of *S. pneumoniae* was used, which was cultured at 37° C. in C+Y medium until a $DO_{550}$ of ≅0.4. The number of cfu ml$^{-1}$ of culture was obtained making serial dilutions of the prior culture in blood agar plates.

Different concentrations of *S. pneumoniae* cells were obtained through serial dilutions in sterile deionized water. An aliquot of 2 µl of each one of the solutions was used as a template for the aDPCR procedure, adding 1.6 µl of the solution (5 µM) of the direct primer, 16 µl of the solution (5 µM) of the reverse biotinylated primer and other components in a final volume of 100 µl following the normal PCR procedure with Taq DNA polymerase. Next, the procedure described in the previous section referring to aPCR was followed.

The amplicons obtained (through aPCR or aDPCR) were observed through electrophoresis in agarose gel (1.5%) through ethidium bromide stain and purified using a commercial kit for the purification of PCR products (Roche.)

The invention claimed is:

1. A method for detecting and/or quantifying *Streptococcus pneumoniae* in at least one biological sample, the method comprising:
   (a) combining superparamagnetic particles (MBs) labeled with a compound A with a DNA probe consisting of SEQ ID NO: 1 labeled on its 5' end with a compound B related to compound A, wherein said MBs bind to said probe via a complex formed by compounds A and B, thereby generating MBs bound to a DNA probe consisting of SEQ ID NO: 1;
   (b) immobilizing the MBs bound to the DNA probe consisting of SEQ ID NO: 1 of step (a) on a solid support, thereby generating immobilized MBs bound to the DNA probe consisting of SEQ ID NO: 1;
   (c) amplifying DNA from at least one biological sample by asymmetric PCR (aPCR) using a primer pair that amplifies the lytA gene of *S. pneumoniae*, wherein the primer pair comprises a direct primer consisting of SEQ ID NO: 3 and a reverse primer consisting of SEQ ID NO: 4, wherein the reverse primer is bound by its 5' end to compound B, thereby generating an aPCR amplicon;
   (d) combining the aPCR amplicon of step (c) with the immobilized MBs bound to the DNA probe consisting of SEQ ID NO: 1 of step (b), wherein said probe hybridizes to said aPCR amplicon, thereby generating a complex;
   (e) adding to the complex of step (d) compound A conjugated to an element capable of being detected and/or quantified by a magneto-amperometric biosensor, wherein said element binds to the complex of step (d) via a complex formed by compounds A and B, thereby generating a complex capable of being detected and/or quantified by a magneto-amperometric biosensor; and
   (f) detecting and/or quantifying a magneto-amperometric signal produced by the complex of step (e), thereby detecting and/or quantifying *Streptococcus pneumoniae* in at least one biological sample.

2. The method according to claim 1, wherein the biological sample is a biological fluid.

3. The method according to claim 2, wherein the biological fluid is blood, cerebrospinal fluid, saliva or urine.

4. The method according to claim 1, wherein said aPCR uses an amount of the direct primer consisting of SEQ ID NO: 3 that is 8 to 12 times smaller than the amount of the reverse primer consisting of SEQ ID NO: 4 bound by its 5' end to compound B.

5. The method according to claim 1, wherein compound A conjugated to an element capable of being detected and/or quantified is covalently conjugated to a hydrophilic polymer backbone.

6. The method according to claim 1, wherein compound A is streptavidin and compound B is biotin.

7. The method according to claim 1, wherein the element capable of being detected and/or quantified is an oxidase enzyme.

8. The method according to claim 7, wherein the oxidase enzyme is a peroxidase and wherein said detection and/or quantification is carried out by adding $H_2O_2$.

* * * * *

SEQUENCE LISTING

<160> NUMBER OF SEQ ID NOS: 16

<210> SEQ ID NO 1
<211> LENGTH: 20
<212> TYPE: DNA
<213> ORGANISM: Streptococcus pneumoniae

<400> SEQUENCE: 1
tgccgaaaac gcttgataca                                                   20

<210> SEQ ID NO 2
<211> LENGTH: 20
<212> TYPE: DNA
<213> ORGANISM: Streptococcus pneumoniae

<400> SEQUENCE: 2
tgtatcaagc gttttcggca                                                   20

<210> SEQ ID NO 3
<211> LENGTH: 20
<212> TYPE: DNA
<213> ORGANISM: Streptococcus pneumoniae

<400> SEQUENCE: 3
ttgggaacgg ttgcatcatg                                                   20

<210> SEQ ID NO 4
<211> LENGTH: 21
<212> TYPE: DNA
<213> ORGANISM: Streptococcus pneumoniae

<400> SEQUENCE: 4
tcgtgcgttt taattccagc t                                                 21

<210> SEQ ID NO 5
<211> LENGTH: 235
<212> TYPE: DNA
<213> ORGANISM: Streptococcus pneumoniae

<400> SEQUENCE: 5
ttgggaacgg ttgcatcatg caggtaggac ctgttgataa tggtgcctgg gacgttgggg       60
gcggttggaa tgctgagacc tatgcagcgg ttgaactgat tgaaagccat tcaaccaaag      120
aagagttcat gacggactac cgcctttata tcgaactctt acgcaatcta gcagatgaag      180
caggtttgcc gaaaacgctt gatacaggga gtttagctgg aattaaaacg cacga           235

<210> SEQ ID NO 6
<211> LENGTH: 24
<212> TYPE: DNA
<213> ORGANISM: Estreptococos del grupo mitis

<400> SEQUENCE: 6
ggtataccga aaacgcttga tact                                              24

<210> SEQ ID NO 7
<211> LENGTH: 24
<212> TYPE: DNA
<213> ORGANISM: Estreptococos del grupo mitis

<400> SEQUENCE: 7
agtatcaagc gttttcggta tacc                                              24

```
<210> SEQ ID NO 8
<211> LENGTH: 23
<212> TYPE: DNA
<213> ORGANISM: Estreptococos del grupo mitis

<400> SEQUENCE: 8
aattgggctt cttttctcac gta                                              23

<210> SEQ ID NO 9
<211> LENGTH: 25
<212> TYPE: DNA
<213> ORGANISM: Estreptococos del grupo mitis

<400> SEQUENCE: 9
tcgtgtgtct tgatacctgc taaat                                            25

<210> SEQ ID NO 10
<211> LENGTH: 259
<212> TYPE: DNA
<213> ORGANISM: Estreptococos del grupo mitis

<400> SEQUENCE: 10
aattgggctt cttttctcac gtagtcggta atggtcgtgt tatgcaggta ggacctgttg      60
ataatggtgc ctgggacgtt ggggggcggtt ggaatgcaga aggttatgca caagttgaac    120
tgattgaaag ccatgaatca aaagaagagt ttctgattga ctatcgtctc tatatcgaac    180
tcttacgcaa tctagcggat gaagctggta taccgaaaac gcttgatact gctgatttag    240
caggtatcaa gacacacga                                                  259

<210> SEQ ID NO 11
<211> LENGTH: 957
<212> TYPE: DNA
<213> ORGANISM: Streptococcus pneumoniae

<400> SEQUENCE: 11
atggaaatta atgtgagtaa attaagaaca gatttgcctc aagtcggcgt gcaaccatat      60
aggcaagtac acgcacactc aactgggaat ccgcattcaa ccgtacagaa tgaagcggat    120
tatcactggc ggaaagaccc agaattaggt tttttctcgc acattgttgg gaacggttgc    180
atcatgcagg taggacctgt tgataatggt gcctgggacg ttgggggcgg ttggaatgct    240
gagacctatg cagcggttga actgattgaa agccattcaa ctaaagaaga gttcatgacg    300
gactaccgcc tttatatcga actcttacgc aatctagcag atgaagcagg tttgccgaaa    360
acgcttgata cagggagttt agctggaatt aaaacgcacg agtattgcac gaataaccaa    420
ccaaacaacc actcagacca tgtggatcca tacccttact tggcaaaatg gggcattagc    480
cgtgagcagt ttaagcatga tattgagaac ggcttgacga ttgaaacagg ctggcagaag    540
aatgacactg gctactggta cgtacactca gacggctctt atccaaaaga caagtttgag    600
aaaatcaatg gcacttggta ctactttgac agttcaggct atatgcttgc agaccgctgg    660
aggaagcaca cagacggcaa ctggtactgg ttcgacaact caggcgaaat ggctacaggc    720
tggaagaaaa tcgctgataa gtggtactat ttcaacgaag aaggtgccat gaagacaggc    780
tgggtcaagt acaaggacac ttggtactac ttagacgcta agaaggcgc catggtatca    840 aatgccttta tccagtcagc ggacggaaca ggctggtact acctcaaacc agacggaaca    900
ctggcagaca agccagaatt cacagtagag ccagatggct tgattacagt aaaataa       957

<210> SEQ ID NO 12
```

<211> LENGTH: 957
<212> TYPE: DNA
<213> ORGANISM: Streptococcus pneumoniae

<400> SEQUENCE: 12

```
atggaaatta atgtgagtaa attaagaaca gatttgcctc aagtcggcgt gcaaccatat    60
aggcaagtac acgcacactc aactgggaat ccgcattcaa ccgtacagaa tgaagcggat   120
tatcactggc ggaaagaccc agaattaggt ttttctcgc acattgttgg gaacggttgc    180
atcatgcagg taggacctgt tgataatggt gcctgggacg ttggggcgg ttggaatgct    240
gagacctatg cagcggttga actgattgaa agccattcaa ctaaagaaga gttcatgacg   300
gactaccgcc tttatatcga actcttacgc aatctagcag atgaagcagg tttgccgaaa   360
acgcttgata cagggagttt agctggaatt aaaacgcacg agtattgcac gaataaccaa   420
ccaaacaacc actcagacca tgtggatcca taccccttact tggcaaaatg gggcattagc   480
cgtgagcagt ttaagtatga tattgagaac ggcttgacga ttgaaacagg ctggcagaag   540
aatgacactg gctactggta cgtacattca gacggctctt atccaaaaga caagtttgag   600
aaaatcaatg gcacttggta ctactttgac agttcaggct atatgcttgc agaccgctgg   660
aggaagcaca cagacggcaa ctggtactgg ttcgacaact caggcgaaat ggctacaggc   720
tggaagaaaa tcgctgataa gtggtactat ttcaacgaag aaggtgccat gaagacaggc   780
tgggtcaagt acaaggacac ttggtactac ttagacgcta agaaggcgc catggtatca    840
aatgcctttta tccagtcagc ggacggaaca ggctggtact acctcaaacc agacggaaca   900
ctggcagaca agccagaatt cacagtagag ccagatggct tgattacagt aaaataa      957
```

<210> SEQ ID NO 13
<211> LENGTH: 957
<212> TYPE: DNA
<213> ORGANISM: Streptococcus pneumoniae

<400> SEQUENCE: 13

```
atggaaatta atgtgagtaa attaagaaca gatttgcctc aagtcggcgt gcaaccatat    60
aggcaagtac acgcacactc aactgggaat ccgcattcaa ccgtacagaa tgaagcggat   120
tatcactggc ggaaagaccc agaattaggt ttttctcgc acattgttgg gaacggttgc    180
atcatgcagg taggacctgt tgataatggt gcctgggacg ttggggcgg ttggaatgct    240
gagacctatg cagcggttga actgattgaa agccattcaa ctaaagaaga gttcatgacg   300
gactaccgcc tttatatcga actcttacgc aatctagcag atgaagcagg tttgccgaaa   360
acgcttgata cagggagttt agctggaatt aaaacgcacg agtattgcac gaataaccaa   420
ccaaacaacc actcagacca tgtggatcca taccccttact tggcaaaatg gggcattagc   480
cgtgagcagt ttaagtatga tattgagaac ggcttgacga ttgaaacagg ctggcagaag   540
aatgacactg gctactggta cgtacattca gacggctctt atccaaaaga caagtttgag   600
aaaatcaatg gcacttggta ctactttgac agttcaggct atatgcttgc agaccgctgg   660
aggaagcaca cagacggcaa ctggtactgg ttcgacaact caggcgaaat ggctacaggc   720
tggaagaaaa tcgctgataa gtggtactat ttcaacgaag aaggtgccat gaagacaggc   780
tgggtcaagt acaaggacac ttggtactac ttagacgcta agaaggcgc catggtatca    840
aatgcctttta tccagtcagc ggacggaaca ggctggtact acctcaaacc agacggaaca   900
ctggcagaca agccagaatt cacagtagag ccagatggct tgattacagt aaaataa      957
```

```
<210> SEQ ID NO 14
<211> LENGTH: 957
<212> TYPE: DNA
<213> ORGANISM: Streptococcus pneumoniae

<400> SEQUENCE: 14
atggaaatta atgtgagtaa attaagaaca gatttgcctc aagtcggcgt gcaaccatat      60
aggcaagtac acgcacactc aactgggaat ccgcattcaa ccgtacagaa tgaagcggat     120
tatcactggc ggaaagaccc agaattaggt tttttctcgc acattgttgg gaacggttgc     180
atcatgcagg taggacctgt tgataatggt gcctgggacg ttggggggcgg ttggaatgct     240 gagacctatg cagcggttga actgattgaa agccattcaa ccaaagaaga gttcatgacg     300
gactaccgcc tttatatcga actcttacgc aatctagcag atgaagcagg tttgccgaaa     360
acgcttgata cagggagttt agctggaatt aaaacgcacg agtattgcac gaataaccaa     420
ccaaacaacc actcagacca cgttgaccct tatccatatc ttgctaaatg gggcattagc     480
cgtgagcagt ttaagcatga tattgagaac ggcttgacga ttgaaacagg ctggcagaag     540
aatgacactg gctactggta cgtacattca gacggctctt atccaaaaga caagtttgag     600
aaaatcaatg gcacttggta ctactttgac agttcaggct atatgcttgc agaccgctgg     660
aggaagcaca cagacggcaa ctggtactgg ttcgacaact caggcgaaat ggctacaggc     720
tggaagaaaa tcgctgataa gtggtactat ttcaacgaag aaggtgccat gaagacaggc     780
tgggtcaagt acaaggacac ttggtactac ttagacgcta agaaggcgc catggtatca      840 aatgccttta tccagtcagc ggacggaaca ggctggtact acctcaaacc agacggaaca     900
ctggcagaca agccagaatt cacagtagag ccagatggct tgattacagt aaaataa       957

<210> SEQ ID NO 15
<211> LENGTH: 957
<212> TYPE: DNA
<213> ORGANISM: Streptococcus pneumoniae

<400> SEQUENCE: 15
atggaaatta atgtgagtaa attaagaaca gatttgcctc aagtcggcgt gcaaccatat      60
aggcaagtac acgcacactc aactgggaat ccgcattcaa ccgtacagaa tgaagcggat     120
tatcactggc ggaaagaccc agaattaggt tttttctcgc acattgttgg gaacggttgc     180
atcatgcagg taggacctgt tgataatggt gcctgggacg ttggggggcgg ttggaatgct     240 gagacctatg cagcggttga actgattgaa agccattcaa ccaaagaaga gttcatgacg     300
gactaccgcc tttatatcga actcttacgc aatctagcag atgaagcagg tttgccgaaa     360
acgcttgata cagggagttt agctggaatt aaaacgcacg agtattgcac gaataaccaa     420
ccaaacaacc actcagacca cgttgaccct tatccatatc ttgctaaatg gggcattagc     480
cgtgagcagt ttaagcatga tattgagaac ggcttgacga ttgaaacagg ctggcagaag     540
aatgacactg gctactggta cgtacattca gacggctctt atccaaaaga caagtttgag     600
aaaatcaatg gcacttggta ctactttgac agttcaggct atatgcttgc agaccgctgg     660
aggaagcaca cagacggcaa ctggtactgg ttcgacaact caggcgaaat ggctacaggc     720
tggaagaaaa ttgctgataa gtggtactat ttcaacgaag aaggtgccat gaagacaggc     780
tgggtcaagt acaaggacac ttggtactac ttagacgcta agaaggcgc catggtatca      840 aatgccttta tccagtcagc ggacggaaca ggctggtact acctcaaacc agacggaaca     900
ctggcagaca agccagaatt cacagtagag ccagatggct tgattacagt aaaataa       957
```

```
<210> SEQ ID NO 16
<211> LENGTH: 957
<212> TYPE: DNA
<213> ORGANISM: Streptococcus pneumoniae

<400> SEQUENCE: 16
atggaaatta atgtgagtaa attaagaaca gatttgcctc aagtcggcgt gcaaccatat      60
aggcaagtac acgcacactc aactgggaat ccgcattcaa ccgtacagaa tgaagcggat     120
tatcactggc ggaaagaccc agaattaggt tttttctcgc acattgttgg gaacggttgc     180
atcatgcagg taggacctgt tgataatggt gcctgggacg ttgggggcgg ttggaatgct     240
gagacctatg cagcggttga actgattgaa agccattcaa ccaaagaaga gttcatgacg     300
gactaccgcc tttatatcga actcttacgc aatctagcag atgaagcagg tttgccgaaa     360
acgcttgata cagggagttt agctggaatt aaaacgcacg agtattgcac gaataaccaa     420
ccaaacaacc actcagacca cgttgaccct tatccatatc ttgctaaatg gggcattagc     480
cgtgagcagt ttaagcatga tattgagaac ggcttgacga ttgaaacagg ctggcagaag     540
aatgacactg gctactggta cgtacattca gacggctctt atccaaaaga caagtttgag     600
aaaatcaatg gcacttggta ctactttgac agttcaggct atatgcttgc agaccgctgg     660
aggaagcaca cagacggcaa ctggtactgg ttcgacaact caggcgaaat ggctacaggc     720
tggaagaaaa tcgctgataa gtggtactat ttcaacgaag aaggtgccat gaagacaggc     780
tgggtcaagt acaaggacac ttggtactac ttagacgcta agaaggcgc catggtatca      840 aatgccttta tccagtcagc ggacggaaca ggctggtact acctcaaacc agacggaaca     900
ctggcagaca agccagactt cacagtagag cctgaaggct tgattacagt aaaataa        957
```